United States Patent [19]
Alig et al.

[11] Patent Number: 5,658,928
[45] Date of Patent: Aug. 19, 1997

[54] AMINO ACID DERIVATIVES

[75] Inventors: Leo Alig, Kaiseraugst; Paul Hadvary, Biel-Benken; Marianne Hürzeler, Däniken; Marcel Müller, Frenkendorf; Beat Steiner, Bättwil; Thomas Weller, Basel, all of Switzerland

[73] Assignee: Hoffmann-La Roche Inc., Nutley, N.J.

[21] Appl. No.: 310,016

[22] Filed: Sep. 21, 1994

Related U.S. Application Data

[62] Division of Ser. No. 854,135, Mar. 19, 1992, Pat. No. 5,378,712.

[30] Foreign Application Priority Data

Mar. 26, 1991 [CH] Switzerland ............... 910/91
Jan. 22, 1992 [CH] Switzerland ............... 176/92

[51] Int. Cl.$^6$ ............... A61K 31/445; C07D 211/56; C07D 211/62; C07D 211/92
[52] U.S. Cl. ............... 514/316; 514/317; 514/318; 546/186; 546/187; 546/193; 546/192
[58] Field of Search ............... 546/187, 193, 546/192; 514/316, 318, 317

[56] References Cited

U.S. PATENT DOCUMENTS

| | | | |
|---|---|---|---|
| 4,618,708 | 10/1986 | Roques et al. | 562/448 |
| 4,738,803 | 4/1988 | Roques et al. | 260/500 SH |
| 4,764,522 | 8/1988 | Imhof et al. | 514/354 |
| 5,039,805 | 8/1991 | Alig et al. | 546/224 |
| 5,084,466 | 1/1992 | Alig et al. | 514/353 |
| 5,134,123 | 7/1992 | Branca et al. | 514/18 |
| 5,389,616 | 2/1995 | Branca et al. | 514/18 |

FOREIGN PATENT DOCUMENTS

| | | |
|---|---|---|
| 91/72086 | 8/1992 | Australia . |
| 2037153 | 9/1991 | Canada . |
| 0 082 088 | 12/1982 | European Pat. Off. . |
| 332008 | 2/1989 | European Pat. Off. . |
| 0372486 | 12/1989 | European Pat. Off. . |
| 0381033 | 1/1990 | European Pat. Off. . |
| 0445796 | 3/1991 | European Pat. Off. . |

OTHER PUBLICATIONS

Analytical Biochemistry 151, 1985, 169–171.
Science 231, 1986, 1559–62.
Chem.Abstr. vol. 92, 1980, 92:208785S.

*Primary Examiner*—Phyllis G. Spivack
*Attorney, Agent, or Firm*—George W. Johnston; Ellen Ciambrone Coletti

[57] ABSTRACT

N-Acyl-α-aminocarboxylic acid derivatives of the formula

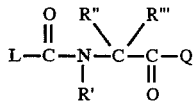

wherein L, R' to R''' and Q have the significance given in the description, can be used for the treatment or prophylaxis of illnesses which are caused by the binding of adhesive proteins to blood platelets and by blood platelet aggregation and cell-cell adhesion.

34 Claims, No Drawings

AMINO ACID DERIVATIVES

This is a division of application Ser. No. 08/854,135 filed Mar. 19, 1992 now U.S. Pat. No. 5,378,712.

BRIEF SUMMARY OF THE INVENTION

The invention relates to N-acyl-α-amino-carboxylic acid derivatives of the formula $$L-\underset{\underset{}{}}{\overset{O}{\overset{\|}{C}}}-\underset{R'}{\overset{R''}{\overset{|}{N}}}-\underset{}{\overset{R''}{\overset{\backslash\;/}{C}}}-\underset{}{\overset{}{\overset{\|}{C}}}-Q \qquad I$$

wherein

L is a group of the formula $$R-\langle\!\!\!\overset{}{\underset{X=Y}{\bigcirc}}\!\!\!\rangle- \qquad L^{1}$$

or $$R^{\circ}-NH(CH_2)_t \qquad L^{2}$$

R is amidino or guanidino, one of X and Y is CH and the other is CH or N, $R^{\circ}$ is hydrogen or amidino, t is an integer between 2 and 6, R', R" and R''' are hydrogen or N-substituents or side-chains usual in α-aminocarboxylic acids, whereby hydroxy or carboxy groups present in R', R" and R''' can be etherified or, respectively, esterified or amidated, and amino groups present in R', R" and R''' can be $C_{1-6}$-alkanoylated or aroylated, wherein R' and R" together with the N atom and C atom to which they are attached can form a 4- to 6- membered ring;

Q is a group of the formula $Q^1$, $Q^2$, $Q^3$, $Q^4$, $Q^5$, $Q^6$, $Q^7$ $$-N(V')(CH_2)_v-C(V'',V''')CH_2OCH_2COO-T \qquad Q^8$$

or, when

R' and R" together with the N atom and C atom to which they are attached form a ring, can also be a group of the formula $Q^9$ n is the number 0 or 1, v is an integer between 0 and 3, T and T' are hydrogen or a lower-alkyl or phenyl-lower-alkyl group which is cleavable under physiological conditions, V to V''' are hydrogen or lower-alkyl, U and U' are hydrogen, $C_{1-6}$-alkanoyl or aroyl, Ar is aryl and $R^2$ to $R^5$ are hydrogen, lower-alkyl, lower-alkoxy, halogen or a group —$OCH_2COO$—T' or $R^2$ and $R^3$ together with the phenyl group to which they are attached form a 1-naphthyl group, as well as hydrates or solvates and physiologically usable salts thereof.

DETAILED DESCRIPTION OF THE INVENTION

The present invention relates to novel N-acyl-α-amino acid derivatives, a process for their preparation, pharmaceutical compositions comprising these compounds, as well as, the use of these compounds in the control or prevention of illnesses, such as, thrombosis, stroke, cardiac infarct, inflammation, and arteriosclerosis. Further, these compounds inhibit metastasis of tumour cells and can be used as antitumor agents. Further, these compounds accelerate wound healing. The compounds can also be used in the treatment of osteoporosis.

The invention relates to N-Aroyl-α-amino-carboxylic acid derivatives of the formula $$L-\underset{\underset{}{}}{\overset{O}{\overset{\|}{C}}}-\underset{R'}{\overset{R''}{\overset{|}{N}}}-\underset{}{\overset{R''}{\overset{\backslash\;/}{C}}}-\underset{}{\overset{}{\overset{\|}{C}}}-Q \qquad I$$

wherein

L is a group of the formula

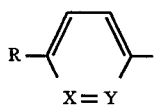 L¹ or

 L²

R is amidino or guanidino, one of X and Y is CH and the other is CH or N,

R° is hydrogen or amidino, t is an integer between 2 and 6,

R', R" and R'" are hydrogen or N-substituents or side-chains usual in α-aminocarboxylic acids, whereby hydroxy or carboxy groups present in R', R" and R'" can be etherified or, respectively, esterified or amidated, and amino groups present in R', R" and R'" can be $C_{1-6}$-alkanoylated or aroylated, wherein R' and R" together with the N atom and C atom to which they are attached can form a 4 to 6 membered ring;

Q is a group of the formula

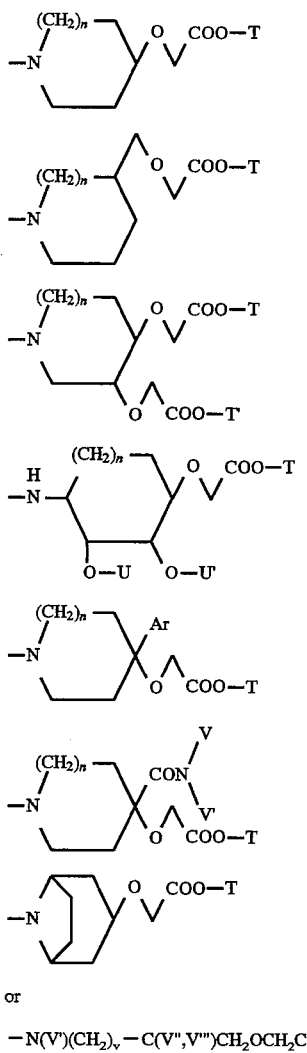

or, where

R' and R" together with the N atom and C atom to which they are attached form a ring, can also be a group of the formula

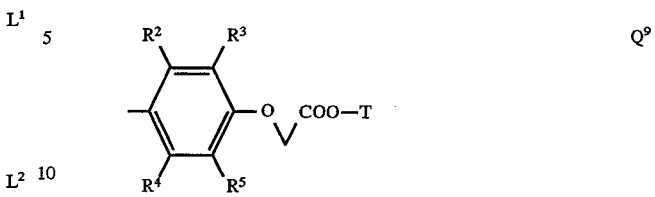 Q⁹ n is the number 0 or 1, v is an integer between 0 and 3,

T and T' are hydrogen or a lower-alkyl or phenyl-lower-alkyl group which is cleavable under physiological conditions, V to V'" are hydrogen or lower-alkyl, U and U' are hydrogen, $C_{1-6}$-alkanoyl or aroyl, Ar is aryl and $R^2$ to $R^5$ are hydrogen, lower-alkyl, lower-alkoxy, halogen or a group —OCH₂COO—T' or $R^2$ and $R^3$ together with the phenyl group to which they are attached form a 1-naphthyl group, as well as hydrates or solvates and physiologically usable salts thereof.

In the scope of the present invention Me denotes methyl, Ac denotes acetyl, tBu denotes t-butyl, Boc denotes t-butoxycarbonyl, Z denotes benzyloxycarbonyl, Fmoc denotes 9-fluorenylmethoxycarbonyl, Val denotes L-valyl, Phe denotes L-phenylalanyl, Ser denotes L-seryl, Gly denotes glycyl, Ala denotes L-alanyl, Asp denotes L-α-aspartyl, Leu denotes L-leucyl, Tyr denotes L-tyrosyl, Sar denotes sarcosyl, Orn denotes L-ornithyl, Lys denotes L-lysyl, Phg denotes L-α-phenylglycyl, Pro denotes L-prolyl, Glu denotes L-glutamyl, Trp denotes L-tryptophanyl.

The term "lower" denotes groups with 1–6, preferably 1–4, C atoms. Methyl, ethyl, propyl, isopropyl, n-, s- or t-butyl, hexyl and the like are examples of lower-alkyl groups. Primary and secondary lower-alkyl groups are examples of lower-alkyl groups which are cleavable under physiological conditions. The term "alkoxy" denotes alkyl ether groups in which the term "alkyl" has the above significance, such as, for example, methoxy, ethoxy, propoxy, isopropoxy, butoxy, isobutoxy and the like.

The symbols R', R" and R'" in the α-aminocarboxylic acid residue —N(R')C(R",R'")CO— represent hydrogen or N-substituents or side-chains usual in open-chain or cyclic, natural or synthetic α-aminocarboxylic acids. Examples of such N-substituents R' and side-chains R" and R'" are lower-alkyl optionally substituted by OH, COOH, NH₂ or aryl, especially by phenyl, hydroxyphenyl, hydroxyiodophenyl or hydroxydiodophenyl. Two lower-alkyl groups R' and R" optionally substituted in this manner can form a 4- to 6-membered, especially a 5- membered, ring together with the N atom and, respectively, C atom to which they are attached. Hydroxy or carboxy groups present in the N-substituents R' and side-chains R" and R'" can be etherified or, respectively, esterified or amidated, and amine groups can be $C_{1-6}$-alkanoylated or aroylated. Examples of such ether, ester and amide groups are —O—T°, —COO—T° and respectively —CON(V,V') in which V and V' have the above significance and T° is lower-alkyl, especially methyl, hexyl and tBu, or aralkyl, especially benzyl.

H-Gly-OH, H-Ala-OH, H-Orn-OH and H-Tyr-OH are examples of open-chain α-aminocarboxylic acids; H-Pro- OH, H-Pro(4-OH)—OH and 2-piperidinecarboxylic acid are examples of cyclic α-aminocarboxylic acids, that is, those in which R' and R'' together with the N atom and, respectively, C atom to which they are attached form a ring.

Formyl, acetyl and propionyl are examples of $C_{1-6}$-alkanoyl groups U and U'. Aryl denotes phenyl optionally having up to 3 substituents such as alkyl, OH, lower-alkoxy, halogen or halo-lower-alkyl, especially $CF_3$. Aroyl denotes the corresponding benzoyl groups.

The compounds of formula I can be solvated, especially hydrated. The hydration can be effected in the course of the manufacturing process or can occur gradually as a consequence of hygroscopic properties of an initially anhydrous compound of formula I.

Examples of physiologically usable salts of the compounds of formula I are salts with physiologically compatible mineral acids such as, for example, hydrochloric acid, sulphuric acid or phosphoric acid; or with organic acids such as, for example, methanesulphonic acid, acetic acid, trifluoroacetic acid, citric acid, fumaric acid, maleic acid, tartaric acid, succinic acid or salicylic acid. The compounds of formula I having a free carboxy group can also form salts with physiologically compatible bases. Examples of such salts are alkali metal, alkaline earth metal, ammonium and alkylammonium salts such as, for example, the Na, K, Ca or tetramethylammonium salt. The compounds of formula I can also be present in the form of zwitterions.

The compounds of formula I which contain one or more asymmetric C atoms can exist as enantiomers, as diastereomers or as mixtures thereof, for example, as racemates.

In formula I, R in a group $L^1$ is preferably amidino, X is preferably CH, Y is preferably CH or N and Q is preferably a group $Q^1$, $Q^2$, $Q^4$, $Q^5$ or $Q^9$.

In the compounds of formula I in which $Q=Q^1$, n is preferably 1, T is preferably hydrogen or methyl and —N(R')C(R'',R''')CO— is preferably one of the residues Gly, Ala, D-Ala, Val, Leu, Sar, Orn, Lys, Phg, 2-methyl-Pro, Phe, Tyr, 3-iodo-Tyr, 3,5-diiodo-Tyr, Ser(Ac), Ser, Asp, Glu, Pro, 4-benzyloxy-Pro, 4-hydroxy-Pro and 2-piperidylenecarbonyl, NHCH($CH_2CH_2NH_2$)CO, Trp, Tyr (Me), Tyr(hexyl), O,N(Me)$_2$-Tyr and N(MeOCH$_2$CH$_2$)Gly.

Preferred compounds with $Q=Q^2$, $Q^4$ or $Q^5$ are those with n=1, T=H; U and U'=H or Ac; Ar=α, α, α-trifluoro-m-tolyl and —N(R')C(R'',R''')CO—=Ala.

Where $Q=Q^9$, $R^2$ to $R^5$ are preferably H or $R^2$ is carboxymethoxy or methoxycarbonylmethoxy, T=H or $CH_3$ and —N(R')C (R'',R''')CO—=Pro.

Examples of preferred compounds are those selected from the group of:

[[1-N-(p-Amidinobenzoyl)-L-alanyl]-4-piperidinyl]oxy]-acetic acid,

[[1-[N-[(5-amidino-2-pyridyl)carbonyl]-L-alanyl]-4-piperidinyl]oxy]acetic acid,

[[1-[N-(p-amidinobenzoyl)-3-(4-hydroxy-3-iodophenyl)-L-alanyl]-4-piperidinyl]oxy]acetic acid,

[[1-[3-acetoxy-N-(p-amidinobenzoyl)-L-alanyl]-4-piperidinyl]oxy]acetic acid,

[p-[[1-(p-amidinobenzoyl)-2-pyrrolidinyl]carbonyl]phenoxy]acetic acid,

[[1-[N-[(5-amidino-2-pyridyl)carbonyl]-L-tyrosyl]-4-piperidinyl]oxy]acetic acid and especially

[[1-N-(p-amidinobenzoyl)-L-tyrosyl]-4-piperidinyl]oxy]-acetic acid.

Further preferred compounds of formula I are those in which Q is a group $Q^3$, especially in which n=0 and T is hydrogen or a group $Q^7$, especially in which T is hydrogen, and those in which Q is a group $Q^8$, especially in which v=1, T is hydrogen or butyl and V' to V''' are hydrogen.

Examples of such compounds are:

(S)-1-[2-(5-Amidinopyridin-2-ylcarbonylamino)-3-(4-methoxyphenyl)propionyl]piperidin-4-yloxyacetic acid, ethyl (S)-1-[2-(4-amidinobenzamido)-3-(4-methoxyphenyl)propionyl]piperidin-4-yloxyacetate, (S)-1-[2-(4-amidinobenzamido)-3-(4-methoxyphenyl) propionyl]piperidin-4-yloxyacetic acid, and

[1-[N-(4-amidinobenzoyl)-4'-hexyloxy-L-phenylalanyl] piperidin-4-yloxy]acetic acid.

The above N-acyl-α-amino acid derivatives can be prepared in accordance with the invention by a) cleaving off an ether group or a protected amino, amidino or guanidino group or a carboxylic acid ester in a compound of the formula

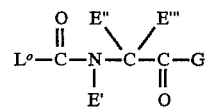

II wherein
$L^o$ is a group of the formula

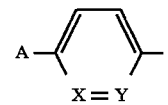

$L^{o1}$ or

$L^{o2}$ in which A is an optionally protected amidino or guanidino group, $R^{o1}$ is an optionally protected amino or guanidino group, E', E'', E''' and G have the same significance as R', R'', R''' and, respectively, Q in formula I, with the proviso that where $R^{o1}$ is amino or guanidino, or where A is amidino or guanidino, at least one of E', E'', E''' and G contains at least one carboxylic acid ester group and/or ether group and/or protected amino group, or b) converting the cyano group in a nitrile of the formula

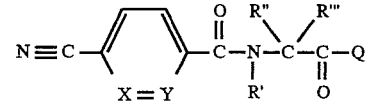

III into the amidino group, or c) reacting an amine of the formula

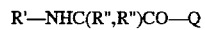

IV with an acid of the formula $L^1$—COOH or a reactive derivative thereof, and d) if desired, functionally modifying a reactive group present in a compound of formula I, and e) if desired, converting a compound of formula I into a physiologically compatible salt or converting a salt of a compound of formula I into the free acid or base.

Examples of cleavable carboxylic acid ester groups are benzyl-OCO— and lower-alkyl-OCO—, such as tBu-OCO—. Examples of cleavable protected amino, amidino and guanidino groups are —NH—Z, —NH—Boc and —N$_3$; —C(NH)NH—Z, —C(NH)NH-Boc, C(N—Boc)N(Boc)$_2$ and —C(N—Boc)NH-Boc; —NHC(NH)NHNO$_2$ and —NHC(N-Boc)NH-Boc. An example of a cleavable ether group is tBu-O—.

Ester groups can be hydrolyzed in a known manner, for example, with a base such as an alkali metal hydroxide, for example, sodium hydroxide, in a solvent such as, for example, methanol or water; or with an acid such as, for example, hydro-chloric acid. Benzyl esters can be cleaved by hydrogenation in the presence of a noble metal catalyst such as, for example, palladium on active charcoal (Pd/C) in a solvent such as, for example, methanol, ethanol, formic acid or acetic acid at a temperature up to about 40° C., preferably at room temperature. An amidino protecting group such as Z present in group A is simultaneously cleaved off.

Ester groups such as tBu-OCO—, as well as amino and amidino protecting groups, such as, Boc and ether groups such as tBu-O— can be cleaved, for example, with an acid, such as, for example, formic acid or trifluoroacetic acid, optionally in a solvent such as, for example, dichloromethane or with glycial acetic acid saturated with HCl at a temperature up to 40° C., preferably at room temperature.

Variant b) can be carried out by converting a nitrile III by reaction with hydrogen sulphide and triethylamine in pyridine into the thioamide, and converting this by methylation with methyl iodide in acetone and subsequent ammonolysis with ammonium acetate in methanol into a compound I.

The coupling c) of the amine IV with the acid L$^1$-COOH or a reactive derivative thereof such as, for example, the acid chloride is carried out in the presence of a base, such as, for example, picoline in a solvent such as dichloromethane at a temperature up to 40° C., preferably at room temperature.

As functional modifications of reactive groups according to process variant d) there are to be named the cleavage of lower-alkoxycarbonyl groups —COO—T or —COO—T or of C$_{1-6}$-alkanoyloxy or aroyloxy groups —O—U or —O—U' present in group Q, or the esterification of a carboxy group in an acid I, and the halogenation, especially the iodination, of an aryl group present in a side-chain R" or R'''.

Thus, butoxycarbonyl or methoxycarbonyl groups present in group Q can be saponified with an acid such as, for example, aqueous acetic acid or acetic acid or under basic conditions, for example, with aqueous sodium hydroxide in methanol and acetoxy groups can be saponified with potassium carbonate in methanol. The esterification of a carboxy group is carried out, for example, by reaction of the acid with a suitable alcohol in the presence of catalytic amounts of H$_2$SO$_4$.

The iodination of an aryl group, especially of the hydroxyphenyl group, in a side-chain R" or R''' can be carried out by reaction of the compound I with Chloramine T followed by sodium iodide in water/dimethylformamide (DMF).

An amine I in which L is a group H$_2$H(CH$_2$)$_r$ is converted into the corresponding guanidine I in which L stands for HN=C(NH$_2$) NH(CH$_2$)$_r$ by reacting the amine with 2-S-isothiourea ethanesulphonate in the presence of a base, such as, Na$_2$CO$_3$ or NaOH at temperatures up to 40° C.

The compounds of formulas II and III are novel and as such are objects of the present invention. They are prepared in a known manner.

Thus, a compound II in which L° stands for an aryl group L$^{01}$ is prepared by reacting an amine of the formula $$E'—NHC(E'',E''')CO—G' \qquad V$$

wherein G' stands for one of the groups Q$^1$ to Q$^9$ in which the group —COO—T and an optionally present —COO—T' group are present as carboxylic acid ester groups, with an acid of the formula

VI or a reactive derivative thereof, for example, the acid chloride.

This reaction can be carried out optionally in the presence of tetra-n-butylammonium hydrogen sulphate, in a solvent such as, for example, dichloromethane and a base such as, for example, aqueous sodium bicarbonate.

An amine H—Q°, wherein Q° stands for one of the amino groups Q$^1$ to Q$^8$ in which the group —COO—T and an optionally present —COO—T' group are present as carboxylic acid ester groups, can be converted with an acid of the formula

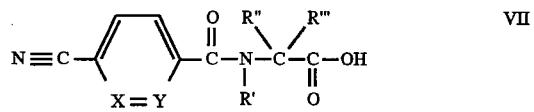

VII into the nitrile III.

This reaction can be carried out in the presence of 2-(1H-benzotriazol-1-yl)-1,1,3,3-tetramethyluronium hexafluorophosphate (HBTU) and an organic base such as N-methylmorpholine in a solvent such as DMF.

A compound II in which A is amidino can be obtained by converting the cyano group into the amidino group in the nitrile corresponding to the compound II. The latter can be prepared by coupling an amine of formula IV above with an acid of the formula

VIII or with a functional derivative thereof, for example, the acid chloride.

This coupling can be carried out in the presence of 2-chloro-4,6-dimethoxy-1,3,5-triazine (CDMT) and a base such as N-methyl morpholine in a solvent such as dichloromethane.

A compound II in which L° stands for a group L$^{02}$ with a protected amino or guanidino group R$^{01}$ is obtained by coupling an amine V with an acid of the formula R$^{01}$—(CH$_2$)$_r$—COOH, for example, in the presence of HBTU and N-methylmorpholine.

A nitrile III in which Q is a group Q$^9$ can be prepared, for example, as follows:

An amine of the formula

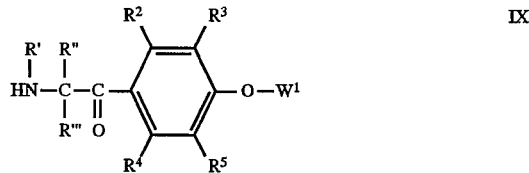

IX wherein R' and R" together with the N atom and C atom form a ring and W$^1$ is a protecting group, is reacted with an acid VIII or a functional derivative thereof, the protecting group is cleaved off and the resulting phenol is treated with a bromoacetic acid derivative BrCH$_2$COO—T.

The reaction of the amine IX with the acid chloride corresponding to the acid VIII can be carried out in the presence of a base such as, for example, triethylamine in DMF. The cleavage of a protecting group $W^1$, for example, benzyl, can be carried out by hydrogen-olysis over Pd/C in ethanol and the reaction of the above phenol with the bromoacetic acid derivative can be carried out in DMF in the presence of potassium carbonate.

The amines IV and V can be prepared, for example, by coupling an N-protected amino acid of the formula $$W^2\text{—N(E')C(E'',E''')COOH} \qquad X$$

with an amine $H\text{—}Q^0$ and removing the protecting group $W^2$, e.g. Z or Boc, in the coupling product.

The acids VII can be prepared by coupling a functional derivative of the acid VIII, for example, the acid chloride, with an amine $$R'\text{—NHC(R'',R''')COO-nieder-Alkyl} \qquad X'$$

and cleaving the ester group in the coupling product. This coupling can be carried out, for example, in dichloromethane in the presence of triethylamine. The lower alkyl group, for example, methyl, can be removed with aqueous LiOH in methanol.

An amino acid of the formula $$R'\text{—NHC(R'',R''')COOH} \qquad X''$$

for example, glycine, can also be converted directly into an acid VII using the acid chloride corresponding to the acid VIII in the presence of aqueous sodium bicarbonate, optionally in the presence of tetramethylammonium sulphate in dichloromethane.

An amine IX can be prepared by reacting the Grignard reagent of a bromide of the formula

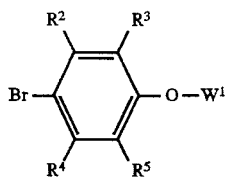

XI with a compound of the formula

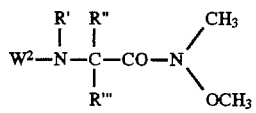

XII and removing the amino protecting group $W^2$ from the reaction product.

The amines $HQ^0$, wherein $Q^0$ stands for one of the amino groups $Q^1$ to $Q^8$ in which the group —COO—T and an optionally present group—COO—T' are present as carboxylic acid ester groups, used above can be prepared as described in Examples 1a)b)c), 2a), 46a)b), 47a) and 48a)b) hereinafter.

The compounds of formula I, their solvates and their salts inhibit not only the binding of fibrinogen, fibrinogen and the Willebrand factor to the fibrinogen receptor of blood platelets (glycoprotein IIb/IIIa), but also the binding of these and further adhesive proteins such as vitronectin, collagen and laminin to the corresponding receptors on the surface of different types of cell. The said compounds therefore influence cell-cell and cell-matrix interactions. In particular, they prevent the formation of blood platelet thrombi and can be used in the control or prevention of illnesses such as thrombosis, stroke, cardiac infarct, inflammation and arteriosclerosis. Further, these compounds have an effect on tumor cells in that they inhibit their metastasis. Accordingly, they can also be used as antitumour agents. Further, they can accelerate the healing of wounds. Since they also prevent bone degradation, they can be used in the treatment of osteoporosis.

The inhibition of the binding of fibrinogen to the fibrinogen receptor, glycoprotein IIb/IIIa, can be demonstrated as follows:

The glycoprotein IIb/IIIa is obtained from Triton X-100 extracts of human blood platelets and purified by lectin affinity chromatography (Analytical Biochemistry 151, 1985, 169–177) and chromatography on an Arg-Gly-Asp-Ser affinity column (Science 231, 1986, 1559–62). The thus-obtained receptor protein is bonded to microtiter plates. The specific binding of fibrinogen to the immobilized receptor is determined with the aid of an ELISA system ("enzyme-linked immunosorbent assay"). The $IC_{50}$ values hereinafter correspond to that concentration of the test substance which is required to inhibit the binding of fibrinogen to the immobilized receptor by 50%:

| Product of Example | 1 | 3 | 4 | 5 | 6 | 7 | 8 | 9 |
|---|---|---|---|---|---|---|---|---|
| $IC_{50}$ (mM) | 0.01 | 0.0017 | 0.14 | 0.001 | 0.027 | 0.033 | 0.008 | 0.08 |
| Product of Example | 10 | 13 | 14 | 15 | 16 | 18 | 21 | 22 |
| $IC_{50}$ (mM) | 0.017 | 0.001 | 0.018 | 0.053 | 0.002 | 0.0017 | 0.16 | 0.47 |
| Product of Example | 24 | 27 | 30 | 37 | 39 | | 40 | 41 |
| $IC_{50}$ (mM) | 0.026 | 0.008 | 0.015 | 0.0003 | 0.0008 | | 0.05 | 0.0007 |
| Product of Example | 42 | 43 | 44 | | | | | |
| $IC_{50}$ (mM) | 0.007 | 0.0016 | 0.01 | | | | | |

These compounds have low toxicity. Thus, the products of Examples 3 and 14 have a $LD_{50}$ of 250 and the product of Example 5 an $LD_{50}$ of 500 mg/kg i.v. in the mouse.

As mentioned earlier, medicaments containing a compound of formula I, a solvate thereof or a salt thereof are an object of the present invention. The medicaments can be administered enterally, for example, orally, in the form of tablets, coated tablets, dragées, hard and soft gelatin capsules; solutions, emulsions or suspensions, or rectally, for example, in the form of suppositories; or as a spray. The administration can, however, also be effected parenterally, for example, in the form of injection solutions or as an infusion.

The active ingredient can be mixed with pharmaceutically inert, inorganic or organic excipients for the preparation of tablets, coated tablets, dragées and hard gelatin capsules. Lactose, maize starch or derivatives thereof, talc, stearic acid or its salts can be used, for example, as such excipients for tablets, dragées and hard gelatin capsules. Suitable excipients for soft gelatin capsules are, for example, vegetable oils, waxes, fats, semi-solid and liquid polyols and the like; depending on the nature of the active ingredient no excipients are, however, generally required in the case of soft gelatin capsules. Suitable excipients for the preparation of solutions and syrups are, for example, water, polyols, saccharose, invert sugar and glucose and the like; suitable excipients for injection solutions are, for example, water, alcohols, polyols, glycerol and vegetable oils and the like.

Suitable excipients for suppositories are, for example, natural or hardened oils, wares, fats and semi-liquid or liquid polyols and the like. The pharmaceutical preparations can, moreover, contain preservatives, solubilizers, stabilizers, wetting agents, emulsifiers, sweeteners, colourants, flavorants, salts for varying the osmotic pressure, buffers, coating agents or antioxidants.

For the control or prevention of the illnesses referred to above, the dosage of the active ingredient can vary within wide limits and will, of course, be fitted to the individual requirements in each particular case. In general, in the case of oral administration a dosage of about 0.1 to 20 mg/kg, preferably of about 0.5 to 4 mg/kg, per day should be appropriate for adults, although the upper limit just given can be exceeded when this is shown to be indicated.

EXAMPLE 1

A solution of 2.43 g of t-butyl [[1-[N-(p-amidinobenzoyl) glycyl]-4-piperidinyl]-oxy]acetate in 15 ml of dichloromethane/trifluoroacetic acid 1:1 is left to stand at room temperature for 5 hours. After evaporation of the solvent and chromatography [silylated silica gel (LiChroprep RP-18), methanol/water gradient] there is obtained 0.46 g of the trifluoroacetate of [[1-[N-(p-amidinobenzoyl)glycyl]-4-piperidinyl]oxy]acetic acid, m.p. 233°–236° C. MS (FAB): 363 (M+H)$^+$.

The starting material can be prepared as follows:

a) 69.1 ml of triethylamine and 70.2 ml of benzyl chloroformate are added in succession at 0° C. to a solution of 50 g of 4-hydroxypiperidine in 500 ml of dichloromethane. The resulting suspension is stirred at room temperature overnight and subsequently filtered. The residue which separates after concentration of the filtrate is taken up in ethyl acetate, washed with water and 1N hydrochloric acid, dried and concentrated. There are obtained 73.6 g of N-benzyloxycarbonyl-4-hydroxy-piperidine, $R_f$=0.56 (ethyl acetate/methanol 9:1), MS (EI): 235 (M$^+$).

b) 28 ml of t-butyl bromoacetate and 1.4 g of tetra-n-butylammonium hydrogen sulphate in 10 ml of water are added to a solution of 30.1 g of N-benzyloxycarbonyl-4-hydroxy-piperidine in 300 ml of toluene. Thereafter, a solution of 125 g of sodium hydroxide in 125 ml of water is added dropwise thereto. After stirring overnight, the organic extracts are separated, dried and concentrated. After drying there are obtained 34.1 g of N-benzyloxycarbonyl-4-[(t-butoxy carbonyl)methoxy]-piperidine, $R_f$=0.76 (ethyl acetate). MS (EI): 293 (M—C$_4$H$_8$)$^+$.

c) 1.5 g of Pd/C (10%) are added to a solution of 30 g of the product from b) in 50 ml of ethanol. The reaction mixture is hydrogenated at room temperature. Thereafter, the catalyst is filtered off, washed with ethanol and the filtrate is concentrated. There are obtained 17.4 g of t-butyl 4-piperidinyloxyacetate, $R_f$=0.14 (ethyl acetate/methanol 1:1). MS (EI): 215 (M$^+$).

d) 5.8 g of Z-glycine are first activated with 5.4 g of CDMT and then coupled with 6.0 g of t-butyl 4-piperidinyloxyacetate and 6.3 ml of N-methylmorpholine in dichloromethane there are obtained 10 g of benzyl [[[4-[(t-butoxycarbonyl) methoxy]piperidinyl]carbonyl]methyl]carbamate. MS (EI): 406 (M$^+$).

e) By hydrogenolyzing a solution of 10 g of the product from d) in 200 ml of ethanol in the presence of 0.7 g of Pd/C (10%) and 1.4 ml of acetic acid there are isolated, after chromatography on silica gel with ethyl acetate/methanol 1:1, 4.1 g of t-butyl 1-[(1-glycyl-4-piperidinyl)oxy]acetate, MS (EI): 273 (M+H$^+$). IR: 1746 cm$^{-1}$.

f) 2.95 g of p-amidinobenzoyl chloride hydrochloride (prepared from p-amidinobenzoic acid by reaction with thionyl chloride in THF in the presence of DMF) are added at room temperature to a mixture of 4.1 g of the product from e) and 0.03 g of tetra-n-butylammonium hydrogen sulphate in 210 ml of dichloromethane/ saturated sodium hydrogen carbonate solution 4:3. After stirring overnight, the mixture is diluted with dichloromethane and water, adjusted to pH 9–10 by the addition of 1N sodium hydroxide solution, the organic extracts are separated, dried and concentrated. After drying, there are obtained 2.43 g of the desired starting material, MS (FAB): 419 (M+H)$^+$.

EXAMPLE 2

A) A solution of 1.5 g of methyl [[1-[N-(p-cyanbenzoyl) glycyl]-4-piperidinyl]oxy]acetate in 215 ml of pyridine/ triethylamine 40:3 is saturated with hydrogen sulphide and left at room temperature for 24 hours. After removing the solvent, the residue is taken up in ethyl acetate and washed with saturated sodium chloride solution. The organic extracts are dried and concentrated. After chromatography of the residue on silica gel with ethyl acetate followed by ethyl acetate/methanol, there are isolated 1.34 g of methyl [[1-[N-[p-(thiocarbamoyl)benzoyl]-glycyl]-4-piperidinyl] oxy]acetate, MS (FAB): 394 (M+H)$^+$.

B) The reaction of 1.25 g of the product of the preceding step with 7.5 ml of methyl iodide in 150 ml of acetone at boiling temperature gives, after filtration and removal of the solvent, 1.65 g of methyl [[1-[N-[p-[1-(methylthio) formimidoyl]benzoyl]-glycyl]-4-piperidinyl]oxy]acetate hydroiodide, MS (FAB): 408 (M+H)$^+$.

C) By ammonolysis of 1.5 g of the product from B) in the presence of 0.32 g of ammonium acetate in 100 ml of methanol at boiling temperature there is obtained 0.76 g of methyl [[1-[N-[p-amidinobenzoyl)glycyl]-4-piperidinyl] oxy]acetate hydroiodide. M.p. 103°–105° C. MS (FAB: 377 (M+H)$^+$.

The nitrile starting material can be prepared as follows:

a) By esterifying the trifluoroacetate of 4-piperidinyloxy-acetic acid (prepared by treating the product of Example 1c) with trifluoroacetic acid in dichloromethane) in methanol in the presence of thionyl chloride there is obtained methyl 4-piperidinyloxyacetate hydrochloride, MS (EI): 173 (M)$^+$.

b) The coupling of 1.35 g of the product from a) with 1.18 g of N-(p-cyanobenzoyl)glycine (prepared by reacting glycine with p-cyanobenzoyl chloride in saturated sodium hydrogen carbonate solution) in the presence of HBTU and N-methylmorpholine in DMF yields, after chromatography on silica gel (ethyl acetate/methanol 9:1 to 1:1), 1.66 g of the desired starting nitrile, MS (EI): 359 (M)$^+$.

EXAMPLE 3

From 13 g of t-butyl [[1-[N-(p-amidinobenzoyl)-L-alanyl]-4-piperidinyl]oxy]acetate there are obtained by treatment with trifluoroacetic acid in dichloromethane (as described in Example 1), after recrystallization from methanol/diethyl ether, 8.9 g of the trifluoroacetate of [[1-[N-(p-amidinobenzoyl)-L-alanyl]-4-piperidinyl]oxy]acetic acid. m.p. 120° C. (decomposition). MS (FAB): 377 (M+H)⁺. $[\alpha]_D^{20}$=+24.7° (c=0.7, water).

The starting material can be prepared as follows:

a) Coupling of 18 g Z-L-alanine with 17.4 g t-butyl 4-piperidinyloxyacetate and subsequent hydrogenolysis of the product obtained as in Example 1d) and e) gives 15.8 g of the acetate of t-butyl 1-[(1-L-alanyl-4-piperidinyl)oxy]acetate. M.p. 93°–96° C. $[\alpha]_D^{20}$=+2.0° (c+1.0 methanol).

b) The coupling of 4.7 g of the product from a) with 3.4 g of p-amidinobenzoyl chloride hydrochloride as in Example 1f) gives 4.2 g of the desired starting material. MS (EI): 433 (M+H)⁺.

EXAMPLE 4

From 0.3 g of t-butyl [[1-[N-(t-butoxycarbonyl)amidinobenzoyl]-D-alanyl]-4-piperidinyl]oxy]acetate there is obtained in analogy to Example 1 0.1 g of [[1-[N-(p-amidinobenzoyl)-D-alanyl]-4-piperidinyl]oxy]acetic acid as the trifluoroacetate. M.p. 115° C. (decomposition). $[\alpha]_D^{20}$=−27.5° (c=0.8, water). MS (FAB): 377 (M+H)⁺.

The starting material can be prepared as follows:

a) By reacting 3 g of t-butyl 4-piperidinyloxyacetate with 2.43 g of Z-D-alanine as described in Example 1d) there are obtained, after chromatography on silica gel with ethyl acetate/hexane 1:1, 3.1 g of benzyl [(R)-1-[[4-[(t-butoxycarbonyl)methoxy]piperidinyl]carbonyl] carbamate. MS (EI): 420 (M)⁺.

b) By hydrogenolyzing 3.1 g of the product from a) as described in Example 1e) there are obtained 2.5 g of the acetate of t-butyl 1-[(1-D-alanyl-4-piperidinyl)oxy] acetate, MS (EI): 215 (M—C₃H₅NO).

c) By reacting 1 g of the product of the previous stage with 0.66 g of p-amidinobenzoyl chloride hydrochloride in DMF in the presence of triethylamine and subsequently treating with di-t-butyl dicarbonate there is obtained, after chromatography on silica gel with dichloromethane/methanol 20:1, 0.3 g of the desired starting material. MS (FAB): 533 (M+H)⁺.

EXAMPLE 5

By hydrolyzing 1.6 g of t-butyl [[1-[N-[(5-amidino-2-pyridyl)carbonyl]-L-alanyl]-4-piperidinyl]oxy]acetate in glacial acetic acid saturated with hydrogen chloride there is obtained, after chromatography on silylated silica gel RP-18 and recrystallization from THF/ethyl acetate, 0.15 g of [[1-[N-[(5-amidino-2-pyridyl)carbonyl]-L-alanyl]-4-piperidinyl]oxy]acetic acid. M.p. above 200° C. (decomposition). MS (FAB): 378 (M+H)⁺.

The starting material can be prepared as follows:

a) By reacting 2.4 g of the acetate of t-butyl 1[(1-L-alanyl-4-piperidinyl)oxy]acetate (Example 3a)) with 1.0 g of 5-cyano-2-picolinic acid in accordance with Example 1d) there are obtained 2.43 g of t-butyl [[1-[N-[(5-cyano-2-pyridyl)carbonyl]-L-alanyl]-4-piperidinyl]oxy]acetate, MS (FAB): 417 (M+H)⁺.

b) The sequential treatment of 2.4 g of the product of the previous stage as described in Example 2A) B) C) yields 2 g of the desired starting material. M.p. 142°–145° C. MS (FAB): 434 (M+H)⁺.

EXAMPLE 6

From 1 g of the acetate of t-butyl [[1-[N-(p-amidinobenzoyl)-L-valyl]-4-piperidinyl]oxy]acetate there is obtained, in analogy to Example 1, after crystallization from ethyl acetate, 0.8 g of [[1-[N-(p-amidinobenzoyl)-L-valyl]-4-piperidinyl]oxy]-acetic acid as the trifluoroacetate. M.p. 210°–211° C. MS (FAB): 405 (M+H⁺). $[\alpha]_D^{20}$=+32.6° (c=0.8, water).

The starting material can be prepared as follows:

a) By coupling 2.5 g of Z-L-valine with 2 g of t-butyl 4-piperidinyloxyacetate as described in Example 2b) there are obtained 4g of t-butyl [[1-[N-[(benzyloxy)carbonyl]-L-valyl]-4-piperidinyl]oxy]acetate, MS (EI): 449 (M+H)⁺.

b) In analogy to Example 1e), but without the addition of acetic acid, from 1.9 g of the product of Example 6a) there are obtained 1.4 g of t-butyl 1-[(1-L-valyl-4-piperidinyl)oxy]-acetate, MS (EI): 315 (M+H)⁺.

c) In analogy to Example 1f), from 3.3 g of the product of Example 6b) and 2.5 g of p-amidinobenzoyl chloride hydro-chloride there are obtained, after chromatography (silica gel; dichloromethane/methanol/acetic acid 95:4:1) and crystallization from diethyl ether, 1.1 g of the desired acetate starting material. M.p. 179°–182° C. MS (FAB): 461 (M+H)⁺.

EXAMPLE 7

From 1.5 g of the acetate of t-butyl [[1-[N-(p-amidinobenzoyl)-L-leucyl]-4-piperidinyl]oxy]acetate there are obtained in analogy to Example 1, after crystallization from ethyl acetate/diethyl ether, 1.1 g of [[1-[N-(p-amidinobenzoyl)-L-leucyl]-4-piperidinyl]oxy]acetic acid as the trifluoroacetate. M.p. 216°–218° C. MS (FAB): 419 (M+H)⁺. $[\alpha]_D^{20}$+22.5° (c=0.8, water).

The acetate starting material can be prepared as follows:

a) By coupling 2.6 g of Z-L-leucine with 2 g of t-butyl 4-piperidinyloxyacetate as described in Example 1d) there are obtained 4.1 g of t-butyl [[1-[N-[(benzyloxy)carbonyl]-L-leucyl]-4-piperidinyl]oxy]acetate, MS (FAB): 463 (M+H)⁺.

b) In analogy to Example 6b) and 1f), from 4.1 g of the product of Example 7a) there are obtained, after chromatography (silica gel; dichloromethane/methanol/acetic acid 95:4:1) and crystallization from diethyl ether, 1.5 g of the desired acetate. M.p. 120°–129° C. (decomposition). MS (FAB): 475 (M+H)⁺.

EXAMPLE 8

From 1.4 g of the acetate of t-butyl [[1-[(p-amidino-N-methylbenzamido)acetyl]-4-piperidinyl]oxy]acetate there is obtained, in analogy to Example 1, after crystallization from diethyl ether, 0.9g of [[1-[(p-amidino-N-methylbenzamido)-acetyl]-4-piperidinyl]oxy]acetic acid as the trifluoroacetate. M.p. 134°–135° C. MS (FAB): 377 (M+H)⁺.

The starting material can be prepared as follows:

a) By coupling 2.0 g of Z-sarcosine N-hydroxysuccinimide ester with 1.3 g of t-butyl 4-piperidinyloxyacetate in the presence of triethylamine in THF there are obtained 2.1 g of benzyl [4-[[[(t-butoxycarbonyl)methoxy]piperidino] carbamoyl]- methyl]methylcarbamate. MS (FAB): 421 (M+H)⁺.

b) In analogy to Example 6b) and 1f), from 4 g of the product of Example 8a) there are obtained, after chromatography (silica gel; dichloromethane/methanol/acetic acid 93:5:2) and crystallization from diethyl ether, 1.5 g of the desired acetate. M.p. 188°–189° C. MS (FAB): 432 (M+H)⁺.

EXAMPLE 9

From 5.4 g of t-butyl [[1-[N$^2$-(p-amidinobenzoyl)-N$^5$-(t-butoxycarbonyl)-L-ornithyl]-4-piperidinyl]oxy]acetate there are obtained in analogy to Example 1 4.9 g of [[1-[N$^2$-(p-amidino-benzoyl)-L-ornithyl]-4-piperidinyl]oxy]acetic acid as the trifluoroacetate. MS (FAB): 420 (M+H)$^+$. [α]$_D^{20}$=+4.5° (c=0.8, MeOH).

The starting material can be prepared as follows:

a) By reacting 6 g of 4-piperidinyloxyacetate with 10.2 g of N$^2$-Z-N$^5$-Boc-L-ornithine as described in Example 1d) there are obtained, after chromatography on silica gel with ethyl acetate/hexane 1:1, 11 g of t-butyl [[1-[N$^2$-(benzyloxycarbonyl)-N$^5$-(t-butoxycarbonyl)-L-ornithyl]-4-piperidinyl]oxy]acetate. MS (FAB): 564 (M+H)$^+$.

b) By hydrogenolyzing 11 g of the product of a) as described in Example 1e), there are obtained 9 g of the acetate of t-butyl [[1-[N$^5$-(t-butoxycarbonyl)-L-ornithyl]-4-piperidinyl]oxy]acetate. MS (FAB): 430 (M+H)$^+$.

c) By reacting 9 g of the product of b) with 4.4 g of p-amidinobenzoyl chloride hydrochloride as described in Example 1f), there are obtained 5.7 g of the desired starting material. MS (FAB): 576 (M+H)$^+$.

EXAMPLE 10

From 0.54 g of t-butyl [[1-[N$^2$-[p-N-(t-butoxycarbonyl)-amidinobenzoyl]-N$^6$-(t-butoxycarbonyl)-L-lysyl]-4-piperidinyl]-oxy]acetate there is obtained in analogy to Example 1, 0.35 g of [[1-[N$^2$-(p-amidinobenzoyl)-L-lysyl]-4-piperidinyloxy]acetic acid as the trifluoroacetate. MS (FAB): 434 (M+H)$^+$. [α]$_D^{20}$=+12.4° (c=0.8, water).

The starting material can be prepared as follows:

a) By reacting 2 g of t-butyl 4-piperidinyloxyacetate with 2.8 g of N$^2$-Z-N$^6$-Boc-L-lysine as described in Example 1d), there are obtained, after chromatography on silica gel with ethyl acetate/hexane 1:1, 2.6 g of t-butyl [[1-[N$^2$-(benzyloxycarbonyl)-N$^6$-(t-butoxycarbonyl)-L-lysyl]-4-piperidinyl]oxy]acetate. MS (FAB): 578 (M+H)$^+$.

b) By hydrogenolyzing 2.6 g of the resulting product as described in Example 1e), there are obtained 2 g of the acetate of t-butyl [[1-[N$^6$-(t-butoxycarbonyl)-L-lysyl]-4-piperidinyl]oxy]-acetate. MS (FAB): 444 (M+H)$^+$.

c) By reacting 2 g of the product of the previous step with 1 g of p-amidinobenzoyl chloride hydrochloride as described in Example 4c), there are obtained, after chromatography (silica gel; dichloromethane/methanol 20:1), 1.95 g of the desired starting material. MS (FAB): 690 (M+H)$^+$.

EXAMPLE 11

From 0.4 g of the acetate of t-butyl [[1-[N-(p-amidinobenzoyl)-L-phenylglycyl]-4-piperidinyl]oxy] acetate there is obtained in analogy to Example 1, 0.25 g of [[1-[N-(p-amidino-benzoyl)-L-phenylglycly]-4-piperidinyl]oxy]acetic acid as the trifluoroacetate. M.p. above 250° C. (ethyl acetate/diethyl ether 1:1). MS (FAB): 439 (M+H)$^+$. [α]$_D^{20}$=+6.5° (c=0.6, MeOH).

The starting material can be prepared as follows:

a) By reacting 1.85 g of t-butyl 4-piperidinyloxyacetate with 3.5 g of Z-L-phenylglycine N-hydroxysuccinimide ester, as described in Example 8a), there are obtained, after chromatography on silica gel with petroleum ether/diethyl ether 1:1, 3.8 g of t-butyl [[1-(N-benzoyloxycarbonyl-L-phenylglycyl)-4-piperidinyl]oxy]acetate. MS (FAB): 349 (M+H)$^+$.

b) By hydrogenolyzing 4.7 g of the resulting product as described in Example 6b), there are obtained 3.2 g of [[1-(L-phenylglycyl)-4-piperidinyl]oxy]acetate. MS (FAB): 349 (M+H)$^+$.

c) By reacting 3.2 g of the product of the previous step with 2.2 g of p-amidinobenzoyl chloride hydrochloride as described in Example 1f), there is obtained, after chromatography (silica gel; dichloromethane/methanol/acetic acid 95:5:2), 0.4 g of the desired acetate. M.p. 207°–220° C. (ethyl acetate, decomposition). MS (FAB): 495 (M+H)$^+$.

EXAMPLE 12

From 0.5 g of the acetate of t-butyl [[1-[1-(p-amidinobenzoyl)-2-methyl-L-prolyl]-4-piperidinyl]oxy] acetate there is obtained, in analogy to Example 1, 0.14 g of [[1-[1-(p-amidinobenzoyl)-2-methyl-L-prolyl]-4-piperidinyl]oxy]acetic acid as the trifluoroacetate. M.p. 219°–220° C. (acetonitrile). MS (FAB): 417 (M+H)$^+$. [α]$_D^{20}$=+17.1° (c=0.9, MeOH).

The acetate starting material can be prepared as follows:

a) By reacting 2-methyl-L-proline hydrobromide with p-cyanobenzoyl chloride analogously to Example 2b) there is obtained 1-(p-cyanobenzoyl)-2-methyl-L-proline. MS (EI): 213 (M—COOH)$^+$.

b) By reacting 1.67 g of t-butyl 4-piperidinyloxyacetate with 0.8 g of the acid chloride of 1-(p-cyanobenzoyl)-2-methyl-L-proline (obtained by treating the product of the previous step with thionyl chloride) there is obtained 0.89 g of t-butyl [[1-[1-(p-cyanobenzoyl)-2-methyl-L-prolyl]-4-piperidinyl]oxy]acetate. M.p. 180°–182° C. (ethyl acetate).

c) By sequentially treating 0.89 g of the product of b), as described in Example 2A)B)C), there is obtained, after chromatography (silylated silica gel RP-18; water/methanol 9:1), 0.59 g of the desired acetate. M.p. 191°–192° C. (ethyl acetate, decomposition). MS (FAB): 473 (M+H)$^+$.

EXAMPLE 13

From 2.5 g of the acetate of t-butyl [[1-[N-(p-amidinobenzoyl)-3-phenyl-L-alanyl]-4-piperidinyl]oxy] acetate, there are obtained, in analogy to Example 1, 1.9 g of [[1-[N-(p-amidinobenzoyl)-3-phenyl-L-alanyl]-4-piperidinyl]oxy]acetic acid as the trifluoroacetate. M.p. 234°–235° C. (ethyl acetate). [α]$_D^{20}$=17.9° (c=1.0, MeOH). MS (EI): 453 (M+H)$^+$.

The acetate starting material can be prepared as follows:

a) By reacting 2.15 g of t-butyl 4-piperidinyloxyacetate with 3.0 g of Z-L-phenylalanine, as described in Example 2b), there are obtained 4.8 g of t-butyl [[1-(N-benzyloxycarbonyl-3-phenyl-L-alanyl)-4-piperidinyl]oxy]acetate MS (FAB): 497 (M+H)$^+$.

b) By hydrogenolyzing 4.8 g of resulting product as described in Example 6b) and subsequently reacting with 2.0 g of p-amidinobenzoyl chloride hydrochloride, as described in Example 1f), there are obtained, after chromatography (silica gel; dichloromethane/methanol/acetic acid 22:2:1) 2.5 g of the desired acetate. M.p. 176°–178° C. (diethyl ether). MS (FAB): 509 (M+H)$^+$.

EXAMPLE 14

From 2.5 g of the acetate of t-butyl [[1-[N-(p-amidinobenzoyl)-3-(p-t-butoxyphenyl)-L-alanyl]-4- piperidinyl]oxy]-acetate there is obtained in analogy to Example 1, after chromatography (silylated silica gel RP-18, water/methanol gradient), 1.0 g of [[1-[N-(p-amidinobenzoyl)-L-tyrosil]-4-piperidinyl]oxy]acetic acid as the trifluoroacetate. M.p. 125°–130° C. (ethyl acetate, decomposition). MS (FAB): 469 (M+H)$^+$.

The acetate starting material can be prepared as follows:

a) By reacting 2.15 g of t-butyl 4-piperidinyloxyacetate with 3.71 g of N-Z-(OtBu)-L-tyrosine as described in Example 2b) there are obtained, after chromatography (silica gel; diethyl ether/petroleum ether 1:1), 4.8 g of t-butyl [[1-[N-(benzyloxy-carbonyl)-3-[p-(t-butoxyphenyl)]-L-alanyl]-4-piperidinyl]oxy]-acetate. M.p. 96° C. (diethyl ether). MS (EI): 417 (M—$C_7H_7$—$C_4H_8$)$^+$, $[\alpha]_D^{20}$=+5.4° (c=0.8, $CH_3OH$).

b) By hydrogenolyzing 4.8 g of the product of the previous step as in Example 6b) and subsequently reacting with 1.5 g of p-amidinobenzoyl chloride hydrochloride, as in Example 1f), there are obtained, after chromatography (silica gel; dichloromethane/methanol/acetic acid 22:2:1), 2.6 g of the desired acetate. M.p. 170°–172° C. (diethyl ether). MS (FAB): 581 (M+H)$^+$.

EXAMPLE 15

0.09 g of the trifluoroacetate of methyl [[1-[N-(p-amidinobenzoyl)-L-tyrosyl]-4-piperidinyl]oxy]acetate is isolated as a byproduct of the chromatography described in Example 14. M.p. 189°–190° C. (ethyl acetate). MS (FAB): 483 (M+H)$^+$.

EXAMPLE 16

By reacting 0.58 g of the trifluoroacetate of [[1-[N-(p-amidinobenzoyl)-L-tyrosyl]-4-piperidinyl]oxy]acetic acid (Example 14) with Chloramine T followed by sodium iodide in water/DMF 8:1 there is obtained, after chromatography (silylated silica gel RP-18 water/acetonitrile gradient), 0.04 g of [[1-[N-(p-amidinobenzoyl)-3-(4-hydroxy-3-iodophenyl)-L-alanyl]-4-piperidinyl]oxy]acetic acid. M.p. 230° C. (water, decomposition). MS (FAB): 595 (M+H)$^+$.

EXAMPLE 17

0.09 g of [[1-[N-(p-amidinobenzoyl)-3-(4-hydroxy-3,5-diiodophenyl)-L-alanyl]-4-piperidinyl]oxy]acetic acid is also isolated from the reaction described in Example 16. M.p. 220°–221° C. (water, decomposition). MS (FAB): 720 (M+H)$^+$.

EXAMPLE 18

From 1.3 g of t-butyl [[1-[3-t-butoxy-N-[p-[N-(t-butoxy carbonyl)amidino]benzoyl]-L-alanyl]-4-piperidinyl]oxy]-acetate by treatment with hydrogen chloride in glacial acetic acid there is obtained, after chromatography (silylated silica gel RP-18, methanol/water gradient) 0.45 g of the hydrochloride of [[1-[3-acetoxy-N-(p-amidinobenzoyl)-L-alanyl]-4-piperidinyl]-oxy]acetic acid. $[\alpha]_D^{20}$=+0.9° (c=1.0, MeOH). MS (FAB): 435 (M+H)$^+$.

The starting material can be prepared as follows:

a) By coupling 7.5 g of Z-L-Ser(tBu)-OH with 7.0 g of t-butyl 4-piperidinyloxyacetate and subsequently hydrogenolyzing the resulting product, as described in Example 1d)e), there are obtained 10.6g of the acetate of t-butyl [[1-(3-t-butoxy-L-alanyl)-4-piperidinyl]oxy] acetate. M.p. 76°–78° C. MS (FAB): 359 (M+H)$^+$.

b) By reacting 9.9 g of the product of the previous step with 5.2 g of p-amidinobenzoyl chloride hydrochloride in DMF in the presence of triethylamine and subsequently treating with di-t-butyl dicarbonate there are obtained, after chromatography on silica gel with dichloromethane/methanol 20:1 followed by ethyl acetate/hexane 3:1, 4.3 g of t-butyl [[1-[3-t-butoxy-N-[p-[N-(t-butoxycarbonyl)amidinobenzoyl]-L-alanyl]-4-piperidinyl]oxyacetate. M.p. 162°–165° C. MS (FAB): 605 (M+H)$^+$.

EXAMPLE 19

From 1.0g of t-butyl [[1-[3-t-butoxy-N-[p-[N-(t-butoxycarbonyl)amidino]benzoyl]-L-alanyl]-4-piperidinyl] oxy]acetate (Example 18) there is obtained in analogy to Example 1, after chromatography (silylated silica gel RP-18, water), 0.58 g of the trifluoroacetate of [[1- [N-(p-amidinobenzoyl)-L-seryl]-4-piperidinyl]oxy]acetic acid. $[\alpha]_D^{20}$=+17.6° (c=1.0, water). MS (FAB): 393 (M+H)$^+$.

EXAMPLE 20

From 5 g of L-N-(p-amidinobenzoyl)-3-[[4-[(t-butoxycarbonyl)methoxy]piperidinyl]carbonyl-β-alanine t-butyl ester there, are obtained in analogy to Example 1, after crystallization using ethyl acetate/THF, 2.0 g of the trifluoroacetate of L-N-(p-amidinobenzoyl)-3-[[4-(carboxymethoxy)piperidino]carbonyl]-β-alanine, m.p. 145°–150° C. MS (FAB): 421 (M+H)$^+$.

The starting material can be prepared as follows:

a) By coupling 11 g of the monohydrate of Z-L-Asp(O-tBu)-OH with 7.0 g of t-butyl 4-piperidinyloxyacetate as described in Example 2b), there are obtained 16 g of L-N-(benzyloxy-carbonyl)-3-[[4-[(t-butoxycarbonyl) methoxy]piperidino]carbonyl]-β-alanine t-butyl ester. MS (FAB): 521 (M+H)$^+$.

b) After hydrogenolyzing 17 g of the product of the previous step, as in Example 6b), there are isolated 11 g of L-3-[[4-[(t-butoxycarbonyl)methoxy]piperidino] carbonyl]-β-alanine t-butyl ester. MS (FAB): 387 (M+H)$^+$.

c) By coupling 11 g of the product of the previous step with 6.9 g of p-amidinobenzoyl chloride hydrochloride, as in Example 1f), there are isolated, after chromatography (silica gel, dichloromethane/methanol 9:1), 10.2 g of the desired starting material. MS (FAB): 533 (M+H)$^+$.

EXAMPLE 21

From 0.5 g of t-butyl [[1-[N-(p-amidinobenzoyl)-4-t-butoxy-L-glutamoyl]-4-piperidinyl]oxy]acetate there is obtained, in analogy to Example 1, after crystallization using ethyl acetate, 0.25 g of the trifluoroacetate of [[1-[N-(p-amidinobenzoyl)-L-α-glutamoyl]-4-piperidinyl]oxy]acetic acid. M.p. 105°–108° C. $[\alpha]_D^{20}$=+6.9°(c=0.8, methanol). MS (FAB): 435 (M+H)$^+$.

The starting material can be prepared as follows:

a) By coupling 11 g of Z-L-Glu(Ot-Bu)-OH with 7.0 g of t-butyl 4-piperidinyloxyacetate, as described in Example 1d), there are obtained 15.4 g of t-butyl [[1-[N-(benzyloxycarbonyl)-4-t-butoxy-L-glutamoyl]-4-piperidinyl]oxy]acetate. MS (FAB): 535 (M+H)$^+$.

b) By hydrogenolyzing 15.4 g of the product of the previous step as in Example 6b), there are obtained 7.5 g of the acetate of t-butyl [[1-(4-t-butoxy-L-glutamoyl]-4-piperidinyl]oxy]acetate. MS (FAB): 401 (M+H)$^+$.

c) By coupling 7.5 g of the product of the previous step with 3.9 g of p-amidinobenzoyl chloride hydrochloride, as in Example 1f), there are obtained 6.9 g of t-butyl [[1-[N-(p-amidinobenzoyl)-4-t-butoxy-L-glutamoyl]-4-piperidinyl]oxy]acetate. MS (FAB): 547 (M+H)$^+$.

EXAMPLE 22

From 2 g of t-butyl [[(R/S)-1-[N-(p-amidinobenzoyl)-L-alanyl]-3-piperidinyl]methoxy]acetate there is obtained, in analogy to Example 1, 0.6 g of the trifluoroacetate of [[(R/S)-1-[N-(p-amidinobenzoyl)-L-alanyl]-3-piperidinyl]methoxy]acetic acid. M.p. 87°–90° C. (ethyl acetate). MS (FAB): 391 (M+H)$^+$.

The starting material can be prepared as follows:

a) From rac-3-(hydroxymethyl)piperidine there is obtained, in analogy to Example 1a), rac-N-benzyloxycarbonyl-3-(hydroxymethyl)piperidine. MS (EI): 249 (M)$^+$.

b) From the product of a) there is obtained, in analogy to Example 1b), benzyl rac-3-[[(t-butoxycarbonyl)methoxy]methyl]-1-piperidinecarboxylate. MS (EI): 307 (M—C$_4$H$_8$)$^+$.

c) The product of b) is hydrogenated, in analogy to Example 1c), to t-butyl rac-(3-piperidinylmethoxy) acetate. MS (EI): 172 (M—C$_4$H$_8$)$^+$.

d) By coupling the product of c) with Z-L-alanine, as in Example 1d), there is obtained benzyl [(S)-1-[[(R/S)-3-[(t-butoxycarbonyl)methoxy]piperidino]carbonyl]ethyl]carbamate. MS (EI): 434 (M)$^+$.

e) By hydrogenating the product of d), as in Example 1e), there is obtained the acetate of t-butyl [[(R/S)-1-L-alanyl-3-piperidinyl]methoxy]acetate. MS (EI): 285 (M—CH$_3$)$^+$.

f) By coupling the product of e) with p-amidinobenzoyl chloride hydrochloride, as in Example 1f), there is obtained, after chromatography (silylated silica gel RP-18), the desired starting material. MS (FAB): 447 (M+H)$^+$.

EXAMPLE 23

From 2.7 g of t-butyl [[1-[N-(p-amidinobenzoyl)-L-alanyl]-4-(α,α,α-trifluoro-m-tolyl)-4-piperidinyl]oxy] acetate there is obtained, in analogy to Example 1, 0.7 g of [[1-[N-(p-amidino-benzoyl)-L-alanyl]-4-(α,α,α-trifluoro-m-tolyl)-4-piperidinyl]-oxy]acetic acid. M.p. above 280° C. (water/methanol). MS (FAB): 521 (M+H)$^+$.

The starting material can be prepared as follows:

a) From 4-(3-(trifluoromethyl)phenyl)piperidin-4-ol there is obtained, in analogy to Example 1a), benzyl 4-hydroxy-4-(α,α,α-trifluoro-m-tolyl)-1-piperidinecarboxylate. MS (EI): 379 (M)$^+$.

b) From the product of a) there is obtained, in analogy to Example 1b), benzyl 4-[(t-butoxycarbonyl)methoxy]-4-(α,α,α-trifluoro-m-tolyl)-1-piperidinecarboxylate. MS (FAB): 494 (M+H)$^+$.

c) By hydrogenating the product of b), as in Example 1e), there is obtained the acetate of [[4-(α,α,α-trifluoro-m-tolyl)-4-piperidinyl]oxy]acetate. MS (EI): 227 (M—C$_6$H$_{12}$O$_3$)$^+$.

d) By coupling the product of c) with Z-L-alanine, as in Example 1d), there is obtained benzyl [(S)-1-[[4-[(t-butoxycarbonyl)methoxy]-4-(α,α,α-trifluoro-m-tolyl)-1-piperidinyl]carbonyl]ethyl]carbamate. MS (FAB): 565 (M+H)$^+$.

e) By hydrogenating the product of d), as in Example 1e), there is obtained the acetate of t-butyl 1-[[L-alanyl-4-(α,α,α-trifluoro-m-toyly)-4-piperidinyl]oxy]acetate. MS (EI): 415 (M—CH$_3$)$^+$.

f) By coupling the product of e) with p-amidinobenzoyl chloride hydrochloride, as in Example 1f), there is obtained the desired starting material. MS (EI): 577 (M+H)$^+$.

EXAMPLE 24

A solution of 150 mg of t-butyl [[1-[1-(p-amidinobenzoyl)-L-propyl]-4-piperidinyl]oxy]acetate in 10 ml of dichloromethane and 10 ml of trifluoroacetic acid is stirred at room temperature for 2 hours and evaporated. The residue is suspended in ether and suction filtered. There are obtained 141 mg of [[1-[1-(p-amidinobenzoyl)-L-propyl]-4-piperidinyl]oxy]acetic acid tri-fluoroacetate. M.p. 234°–236° C.

The starting material can be prepared as follows:

a) 4.97 g of 4-cyanobenzoyl chloride, 3.45 g of L-proline and 0.73 g of tetramethylammonium sulphate in 300 ml of dichloromethane and 150 ml of 5% sodium hydrogen carbonate solution are stirred for 48 hours. The aqueous phase is acidified with 3N sulphuric acid and extracted with ethyl acetate. The ethyl acetate phase is washed with saturated sodium chloride solution, dried and evaporated. Chromatography of the residue on silica gel (RP-18) using water gives 3.70 g of 1-(p-cyanobenzoyl)-L-proline. M.p. 80°–85° C.

b) Coupling of 250 mg of 1-(p-cyanobenzoyl)-L-proline with 215 mg of t-butyl 4-piperidinyloxyacetate gives, after chromatography on silica gel with ethyl acetate/methanol (98:2), 300 mg of t-butyl [[1-[1-(p-cyanobenzoyl)-L-prolyl]-4-piperidinyl]oxy]acetate. MS: 422 (M+H)$^+$.

c) Treatment of 1 g of the product of the previous step, as in Example 2A)B)C), leads via t-butyl [[1-[1-(p-thiocarbamoyl)benzoyl]-L-prolyl]-4-piperidinyl]oxy] acetate, m.p. 108°–110° C., to 72 mg of the desired acetate, m.p. 100° C. (decomposition).

EXAMPLE 25

Analogously to Example 24, from 150 mg of t-butyl [[1-[(4R)-1-(p-amidinobenzoyl)-4-benzyloxy-L-prolyl]-4-piperidinyl]oxy]acetate hydroiodide there are obtained, after chromatography on silica gel (RP-18, water/THF 95:5), 72 mg of [[1-[(4R)-1-(p-amidinobenzoyl)-4-benzyloxy-L-prolyl]-4-piperidinyl]oxy]acetic acid. M.p. 226°–227° C.

The acetate starting material can be prepared as follows:

a) 1.46 ml of triethylamine are added to a solution of 905 mg of (4R)-hydroxy-L-proline methyl ester and 828 mg of 4-cyanobenzoyl chloride in 50 ml of dichloromethane. After stirring, the solution is washed with saturated sodium chloride solution, dried and evaporated. Chromatography of the residue on silica gel (ethyl acetate/hexane 5:1) gives 810 mg of (4R)-1-(p-cyano-benzoyl)-4-hydroxy-L-proline ester. M.p. 101°–102° C.

b) 40 µl of trifluoromethanesulphonic acid are added dropwise to a solution of 730 mg of the previous step and 600 µl of benzyl trichloroacetimidate in 5 ml of cyclohexane and 5 ml of dichloromethane. The resulting precipitate is filtered off under suction and the filtrate is washed with 5% sodium hydrogen carbonate solution, dried and evaporated. Chromatography of the residue on silica gel (ethyl acetate) gives 940 mg of (4R)-4-benzyloxyl-1-(p-cyano-benzoyl)-L-proline methyl ester. MS: 305 (M-59).

c) 880 mg of the product of the previous step and 1.2 ml of 2N lithium hydroxide solution are stirred in 10 ml of methanol. After removing the methanol, the aqueous residue is acidified with 2.4 of 1N hydrochloric acid and extracted with ethyl acetate. Drying of the organic phase and evaporation gives 470 mg of (4R)-4-benzyloxy-1-(p-cyanobenzoyl)-L-proline. M.p. 58°–60° C.

d) 450 mg of the product of c) are coupled with 280 mg of t-butyl 4-piperidinyloxyacetate in the presence of HBTU. The residue is dissolved in ethyl acetate and the ethyl acetate phase is washed with 5% sodium hydrogen carbonate solution, 1N potassium hydrogen sulphate solution and saturated sodium chloride solution, dried and evaporated. After chromatography of the residue on silica gel (dichloromethane/methanol 98:2) there are obtained 500 mg of t-butyl [[1-[(4R)-4-benzyloxy-1-(p-cyanobenzoyl)-L-prolyl]-4-piperidinyl]oxy]acetate. MS: 548 (M+H)$^+$.

e) Treatment of 400 mg of the product of the previous step, as in Example 2A)B)C), leads to 177 mg of the desired acetate. M.p. of the hydroiodide 148°–150° C.

EXAMPLE 26

A solution of 1.60 g of t-butyl [[1-[(4R)-1-(p-amidinobenzoyl)-4-hydroxy-L-prolyl]-4-piperidinyl]oxy]acetate in 20 ml of dichloromethane and 20 ml of trifluoroacetic acid is stirred at room temperature for 2 hours and evaporated. The residue is dissolved in ethanol and treated with ether. Suction filtration and drying of the precipitate gives 1.25 g of [[1-[(4R)-1-(p-amidinobenzoyl)-4-hydroxy-L-prolyl]-4-piperidinyl]oxy]acetic acid trifluoroacetate. M.p. 220° C.

The acetate starting material can be prepared as follows:

a) Coupling of 14.78 g of (4R)-1-(benzyloxycarbonyl)-4-hydroxy-L-proline with 12.0 g of t-butyl 4-piperidinyloxyacetate gives, after chromatography on silica gel (ethyl acetate/methanol 95:5), 17.83 g of t-butyl [[1-[(4R)-1-(benzyloxycarbonyl)-4-hydroxy-L-prolyl]-4-piperidinyl]oxy]acetate. MS: 463 (M+H)$^+$.

b) Hydrogenation of 17.0 g of the product of the preceding step in ethanol in the presence of 2.0 g of Pd/C (10%) gives, after filtration of the catalyst and concentration, 11.06 g of t-butyl [[1-[(4R)-4-hydroxy-L-prolyl]-4-piperidinyl]oxy]acetate. MS: 329 (M+H)$^+$.

c) Reaction of 2.0 g of the product of the previous step with 1.34 g of p-amidinobenzoyl chloride according to Example 1f) gives 1.95 g of the desired acetate.

EXAMPLE 27

A solution of 700 mg of t-butyl [[1-[[1-(p-amidinobenzoyl)-2-piperidinyl]carbonyl]-4-piperidinyl] oxy]acetate in 20ml of dichloromethane and 20 ml of trifluoroacetic acid is stirred at room temperature for 3 hours and evaporated. The residue is dissolved in ethanol and treated with ether. Suction filtration and drying of the precipitate and chromatography on silica gel (RP-18, water/ THF 9:1) gives 111 mg of [[1-[[1-(p-amidinobenzoyl)-2-piperidinyl]carbonyl]-4-piperidinyl]oxyacetic acid. M.p. 233°–234° C.

The acetate starting material is prepared as follows:

a) Coupling of 5.26 g of 1-(benzoyloxycarbonyl)-2-piperidinecarboxylic acid with 4.30 g of t-butyl 4-piperidinyloxyacetate and chromatography on silica gel (ethyl acetate/hexane 2:1) gives 7.33 g of benzyl 2-[[4-[(t-butoxycarbonyl)methoxy]piperidino]-carbonyl]-1-piperidinecarboxlate. MS: 461 (M+H)$^+$.

b) Hydrogenation of 4.6 g of the product of the previous step in the presence of 0.4 g of Pd/C (10%) gives, after filtration of the catalyst and concentration of the solvent, 3.2 g of t-butyl [[1-(2-piperidinylcarbonyl)-4-piperidinyl]oxy]acetate. MS: 327 (M+H)$^+$.

c) Reaction of 3.26 g of the product of the previous step with 2.49 g of p-amidinobenzoyl chloride according to Example 1f) gives 1.56 g of the desired acetate, m.p. 93°–95° C.

EXAMPLE 28

A solution of 130 mg of t-butyl [[(1RS,2RS,3RS,4SR)-[[N-(p-amidinobenzoyl)-L-alanyl]amino]-2,3-diacetoxycyclohexyl]-oxy]acetate hydrochloride in 5 ml of dichloromethane and 5 ml of trifluoroacetic acid is stirred at room temperature for 2 hours and concentrated. Suspension of the residue in ether and suction filtration gives 126 mg of [[(1RS,2RS,3RS,4SR)-4-[[N-(amidinobenzoyl)-L-alanyl] amino]-2,3-diacetoxycyclohexyl]oxy]-acetic acid trifluoroacetate. MS: 507 (M+H)$^+$.

The starting material is prepared as follows:

a) A solution of 4.64 g of cis-4-amino-2-cyclohexen-1-ol, 10.2 g of N-(benzyloxycarbonyloxy)succinimide and 5.7 ml of triethylamine in DMF is diluted with ether after stirring, washed with saturated sodium chloride solution, dried and concentrated. Chromatography of the residue on silica gel (ethyl acetate/hexane 2:1) gives 5.62 g of benzyl (1RS,4SR)-4-hydroxy-2-cyclohexene-1-carbamate. MS: 156 (M+H)$^+$.

b) 2.1 g of the product of the previous step are reacted with 1.76 ml of t-butyl bromoacetate under phase transfer conditions (30 ml of toluene, 30 ml of 50% sodium hydroxide solution, 100 mg of tetrabutylammonium hydrogen sulphate). After stirring, the organic phase is separated, washed with saturated sodium chloride solution, dried and concentrated. Chromatography of the residue on silica gel (hexane/ethyl acetate 3:1) gives 1.91 g of benzyl (1RS ,4SR)-4-[(t-butoxycarbonyl)methoxy]-2-cyclohexene-1-carbamate. MS: 333 (M-28)$^+$.

c) A solution of 722 mg of the product of the previous step, 280 mg of N-ethylmorpholine N-oxide and 26 mg of osmium tetroxide in 20 ml of acetone and 10 ml of water is stirred and then the acetone is removed under reduced pressure and the aqueous phase is extracted with ether. Washing the organic phase with saturated sodium chloride solution, drying and concentration gives, after chromatography on silica gel (ethyl acetate/ hexane 2:1), 476 mg of benzyl (1RS,2RS,3SR,4SR)-4-[(t-butoxycarbonyl)methoxy]-2,3-dihydroxycyclohexanecarbamate. MS: 396 (M+H)$^+$.

d) A solution of 728 g of the product of the previous step in 10 ml of ethanol is hydrogenated in the presence of 100 mg of 10% Pd/C. Then, the catalyst is filtered off, the filtrate is evaporated and the residue is coupled with 410 mg of N-benzyloxycarbonyl-L-alanine in 30 ml of THF in the presence of 697 mg of HBTU and 200 µl of triethylamine. The reaction solution is diluted with ether, washed with saturated sodium bicarbonate solution and saturated sodium chloride solution, dried and concentrated. Chromatography on silica gel (ethyl acetate/methanol 95:5) gives 521 mg of benzyl [(S)-1-

[[(1RS,2SR,3SR,4SR)-4-[(t-butoxycarbonyl)methoxy]-2,3-dihydroxy-cyclohexyl]carbamoyl]ethyl]carbamate. MS: 467 (M+H)$^+$.

e) Acetylation of 800 mg of the product of the previous step in 10 ml of acetic anhydride and 10 ml of pyridine and concentration of the reaction solution gives, after chromatography on silica gel (ethyl acetate/hexane 2:1), 670 mg of benzyl [(S)-I-[[(1RS,2SR,3SR, 4SR)-4-[(t-butoxycarbonyl)methoxy]-2,3-acetoxycyclohexyl]carbamoyl]ethyl]carbamate. MS: 551 (M+H)$^+$.

f) Hydrogenation of 670 mg of the product of the previous step in 10 ml of ethanol in the presence of 100 mg of 10% Pd/C, filtration of the catalyst and evaporation of the solution gives, after treatment (analogously to Example 1f)) with 329 mg of p-amidinobenzoyl chloride and chromatography on silica gel (RP-18, water/methanol 9:1), 230 mg of the desired starting material. MS: 563 (M+H)$^+$.

EXAMPLE 29

220 mg of the product of Example 28 and 300 mg of potassium carbonate in 10 ml of methanol are stirred at room temperature and the methanol is then evaporated. Chromatography on silica gel (RP-18, water/acetonitrile 95:5) gives 110 mg of [[(1RS ,2RS ,3RS ,4SR)-4-[[N-(p-amidinobenzoyl)-L-alanyl]amino]-2,3-dihydroxycyclohexyl]oxy]acetic acid.

EXAMPLE 30

Treatment of 1.3 g of methyl rac-[p-[[1-(p-cyanobenzoyl)-2-pyrrolidinyl]carbonyl]phenoxy]acetate as described in Example 2A)B)C) gives, after chromatography (silylated silica gel RP-18, water/methanol gradient) and recrystallization from ethanol, 0.45 g of the acetate of methyl rac-[p-[[1-(p-amidinobenzoyl)-2-pyrrolidinyl]carbonyl]phenoxy]acetate. M.p. 210°–211° C. MS (FAB): 410 (M+H)$^+$.

The starting material can be prepared as follows:

a) By reacting the Grignard reagent from 8.3 g of p-benzyloxybromobenzene and 0.8 g of magnesium shavings with Z-L-proline N-methoxymethylamide in THF there are isolated, after chromatography (silica gel, diethyl ether/petroleum ether 1:1), 4.3 g of rac-1-(benzyloxycarbonyl)-2-(p-benzyloxybenzoyl)-pyrrolidine. MS (EI): 211 ($C_{14}H_{11}O_2$)$^+$, 204 ($C_{12}H_{14}O_2$)$^+$.

b) By hydrogenating 3.3 g of the product of the previous step as in Example 6b) and subsequently reacting with 1.32 g of p-cyanobenzoyl chloride in DMF in the presence of triethylamine there are obtained 2.8 g of rac-1-(p-cyanobenzoyl)-2-(p-hydroxybenzoyl)-pyrrolidine. M.p. 194°–196° C. (ethyl acetate). MS (EI): 320 (M)$^+$.

c) Reaction of 2.8 g of the product of the previous step with 1.53 g of methyl bromoacetate in DMF in the presence of potassium carbonate gives, after chromatography (silica gel, dichloromethane/methanol 99:1), 1.3 g of the desired starting material. MS (EI): 39:2 (M)$^+$.

EXAMPLE 31

By heating 0.30 g of the product of Example 30 in aqueous acetic acid there is obtained, after chromatography (silylated silica gel RP-18, water/acetonitrile gradient), 0.11 g of rac-[[[1-(p-amidinobenzoyl)-2-pyrrolidinyl]carbonyl] phenoxy]acetic acid. M.p. above 250° C. MS (FAB): 396 (M+H)$^+$.

EXAMPLE 32

By treating 0.85 g of dimethyl [[4-[1-(p-cyanobenzoyl)-DL-prolyl]-m-phenylene]dioxy]dicetate, as described in Example 2A)B)C), there is obtained, after chromatography (silylated silica gel RP-18, water/methanol gradient) and crystallization from diethyl ether, 0.09 g of the acetate of dimethyl [[4-[1;(p-amidinobenzoyl)-DL-prolyl]-m-phenylene]dioxy]diacetate. M.p. 93°–95° C. MS (FAB): 498 (M+H)$^+$.

The starting material can be prepared as follows:

a) By reacting the magnesium salt of 4 g of methyl 3-hydroxyphenoxyacetate with 5.8 g of Z-L-prolinal and etherifing the product with 3.8 g of methyl bromoacetate as described in Example 30c) there are obtained, after chromatography (silica gel, diethyl ether/petroleum ether 4:1), 7.6 g of dimethyl [[4-[(RS)-[1-(benzyloxycarbonyl)-DL-pyrrolyl]hydroxymethyl]-m-phenylene]dioxy]diacetate. MS (FAB): 488 (M+H)$^+$.

b) From 5.3 g of the product of the previous step there are obtained by oxidation with 7.5 ml of Jones reagent in diethyl ether, after chromatography (silica gel, dichloromethane/methanol 99:1), 2.2 g of dimethyl [[4-[1-(benzyloxycarbonyl)-DL-prolyl]-m-phenylene] dioxy]diacetate. MS (EI): 485 (M)$^+$.

c) By hydrogenating of 2.2 g of the product of the previous step as in Example 6b) and subsequently reacting with 1.0 g of p-cyano benzoyl chloride in chloroform in the presence of triethylamine there is obtained, after chromatography (silica gel, dichloromethane/methanol 99:1), 0.85 g of the desired starting material. MS (EI): 480 (M)$^+$.

EXAMPLE 33

From 0.09 g of the product of Example 32 there is obtained by hydrolysis using aqueous sodium hydroxide in methanol at 50° C. after neutralization with acetic acid, chromatography (silylated silica gel RP-18, water/acetonitrile gradient) and crystallization from ethanol 0.09 g of the monosodium salt of [[4-[1-(p-amidinobenzoyl)-DL-prolyl]-m-phenylene]dioxy]acetic acid. M.p. 241–242° C. MS (FAB): 492 (M+Na)$^+$, 470 (M+H)$^+$.

EXAMPLE 34

From 0.47 g of [[1-[N-(p-amidinobenzoyl)-L-tyrosyl]-4-piperidinyl]oxy]acetic acid (Example 14) there is obtained by esterification in ethanol in the presence of catalytic amounts of conc. sulphuric acid, after chromatography (LiChroprep RP-18, water/ethanol gradient) 0.3 g of ethyl [[1-[N-(p-amidinobenzoyl)-L-tyrosyl]-4-piperidinyl]oxy] acetate hemisulphate, m.p. 182–184° C. (ethanol). MS (ISO=Ionspray): 497 (M+H)$^+$.

EXAMPLE 35

From 0.48 g of t-butyl [[1-[N-[5-(1-t-butoxyformamido) pentanoyl]-3-(p-t-butoxyphenyl)-L-alanyl]-4-piperidinyl] oxy]acetate there is obtained, in analogy to Example 1, after crystallization from diethyl ether, 0.2 g of the trifluoroacetate salt of [[1-[N-(5-aminopentanoyl)-L-tyrosyl]-4-piperidinyl]oxy]-acetic acid, m.p. 78°–88° C. (decomposition). $[\alpha]_D^{20}$=+11.6° (c=0.7, methanol). MS (FAB): 422 (M+H)$^+$.

The ester starting material can be prepared as follows:

The reaction of 0.7 g of t-butyl [[1-[3-(p-t-butoxyphenyl)-L-alanyl]-4-piperidinyl]oxy]acetate (prepared by hydrogenolysis of the produce of Example 14a) with 0.35 g of N-Boc-5-amino-pentanoic acid in the presence of HBTU and N-methylmorpholine (as in Example 2b) yields 0.55 g of ester starting material, $[\alpha]_D^{20}=+1.2°$ (c=0.4, methanol). MS (FAB): 634 (M+H)$^+$.

EXAMPLE 36

From 0.6 g of [(S)-3-(p-amidinobenzamido)-3-[[4-[(t-butoxycarbonyl)methoxy]piperidino]carbonyl]propyl]t-butylcarbamate there is obtained in analogy to Example 1, after chromatography (LiChroprep RP-18, water/methanol gradient) and trituration in THF, 0.26 g of the trifluoroacetate salt of [[1-[(S)-2-(p-amidinobenzamido)-4-aminobutanoyl]-4-piperidinyl]oxy]-acetic acid. M.p. above 170° C. (decomposition). $[\alpha]_D^{20}=+5.8°$ (c=0.5, water). MS (EI): 406 (M+H)$^+$.

The starting material can be prepared as follows:

a) The reaction of 1.0 g of t-butyl 4-piperidinyloxyacetate with 2.0 g of $N^2$-Fmoc-$N^4$-Boc-(S)-2,4-diaminobutyric acid in the presence of HBTU and Hünig's base as described in Example 2b) yields, after chromatography (silica gel EtOAc/hexane 1:1.5), 2.2 g of 3-t-butyl-1-(fluoren-9-ylmethyl)-(S)-1-[[4-[(t-butoxycarbonyl)methoxy]piperidino]carbonyl] trimethylenedicarbamate, MS (FAB): 638 (M+H)$^+$.

b) Reaction of 2.3 g of the product of a) with piperidine (20% in DMF) gives, after chromatography (silica gel, ethyl acetate/methanol 4:1), 0.65 g of t-butyl [(S)-3-amino-3-[[4-[(t-butoxycarbonyl)methoxy]piperidino]carbonyl]propyl]-carbamate, MS (FAB): 416 (M+H)$^+$.

c) By reacting 0.65 g of the product of b) with 0.38 g of p-amidinobenzoyl chloride hydrochloride (as in Example 1f) there is obtained 0.6 g of the carbamate starting material, MS (FAB): 562 (M+H)$^+$.

EXAMPLE 37

From 0.25 g of the acetate salt of t-butyl [[1-[N-[(5-amidino-2-pyridyl)carbonyl]-3-(p-t-butoxyphenyl)-L-alanyl]-4-piperidinyl]oxy]acetic acid there is obtained (as in Example 1), after chromatography (LiChroprep RP-18, water/methanol gradient) and trituration in ethyl acetate, 0.12 g of [[1-[N-[(5-amidino-2-pyridyl)carbonyl]-L-tyrosyl]-4-piperidinyl]oxy]acetic acid, m.p. 198°–200° C. (decomposition). MS (FAB): 470 (M+H)$^+$.

The starting material can be prepared as follows:

a) Reaction of 2.5 g of t-butyl [[1-[3-(p-t-butoxyphenyl)-L-alanyl]-4-piperidinyl]oxy]acetate with 0.85 g of 5-cyano-2-picolinic acid (as in Example 1d) yields 1.55 g of t-butyl [[1-[3-(p-t-butoxyphenyl)-N-[[5-cyano-2-pyridyl]carbonyl]-L-alanyl]-4-piperidinyl]oxy]acetate. M.p. 122–123° C. (diethyl ether/petroleum ether 4:1). MS (FAB): 565 (M+H)$^+$.

b) The successive treatment of 1.43 g of the product of the previous step as described in Example 2a)b)c) yields 0.98 g of the desired starting material. M.p. 183–186° C. MS (EI): 582 (M+H)$^+$.

EXAMPLE 38

Reaction of 0.7 g of ethyl (S)-1-[2-(5-cyanopyridin-2-ylcarbonylamino)-3-(4-methoxyphenyl)propionyl] piperidin-4-yloxyacetate as described in Example 2A)B)C) yields, after crystallization from water, 0.1 g of the acetate salt of ethyl (S)-1-[2-(5-amidinopyridin-2-ylcarbonylamino)-3-(4-methoxyphenyl)propionyl]piperidin-4-yloxyacetate. M.p. 180°–181 ° C. (decomposition). MS (ISP): 512 (M+H)$^+$ The nitrile starting material can be prepared as follows:

a) Reaction of 7 g of N-Z-L-tyrosine dihydrate with 4.5 g of ethyl 4-piperidinyloxyacetate [obtained by treating the corresponding t-butyl ester, Example 1c), with trifluoroacetic acid followed by ethanolic hydrochloric acid] as in Example d) yields 6.5 g of ethyl [[1-[N-(benzyloxycarbonyl)-L-tyrosyl]-4-piperidinyl]oxy] acetate. This product is treated with methyl iodide in DMF in the presence of potassium carbonate, whereby there are obtained after chromatography (silica gel, methylene chloride/methanol 99:1) 4.2g of ethyl (S)-1-[2-benzyloxycarbonylamino-3-(4-methoxyphenyl) propionyl]piperidin-4-yloxyacetate, $[\alpha]_D^{20}=+1.9°$ (c=0.8, methanol). MS (ISP): 499 (M+H)$^+$.

b) From 4 g of the product of a) there are obtained, in analogy to Example 1e), 3.5 g of ethyl (S)-1-[2-amino-3-(4-methoxyphenyl)propionyl]piperidin-4-yloxyacetate, MS (EI): 365 (M+H)$^+$.

c) Coupling of 1.46 g of the product of b) with 0.74 g of 5-cyano-2-picolinic acid in accordance with Example 1 d) gives, after chromatography on silica gel (methylene chloride/methanol 40:1), 0.72 g of nitrile starting material, MS (ISP): 495.5 (M+H)$^+$.

EXAMPLE 39

By saponifying ethyl (S)-1-[2-(5-amidinopyridin-2-ylcarbonylamino)-3-(4-methoxyphenyl)propionyl] piperidin-4-yloxyacetate (Example 38) at pH=12 there is obtained, after chromatography (LiChroprep RP-18, water/methanol gradient) and trituration in ethanol, (S)-1-[2-(5-amidinopyridin-2-ylcarbonylamino)-3-(4-methoxyphenyl) propionyl]piperidin-4-yloxyacetic acid. M.p. above 250° C. MS (ISP): 484.4 (M+H)$^+$.

EXAMPLE 40

By coupling 1.2 g of ethyl (S)-1-[2-amino-3-(4-methoxyphenyl)propionyl]piperidin-4-yloxacetate (Example 38b) with 0.77 g of 4-amidinobenzoyl chloride hydrochloride in 3-picoline analogously to Example 1f), there is obtained, after chromatography (LiChroprep RP-18, water/ethanol gradient) and trituration with ethyl acetate, 0.25 g of the hydrochloride of ethyl (S)-1-[2-(4-amidinobenzamido)-3-(4-methoxyphenyl)propionyl] piperidin-4-yloxyacetate m.p. 105°–107° C. MS (ISP): 511.3 (M+H)$^+$.

EXAMPLE 41

By saponifying 0.35 g of the hydrochloride of ethyl (S)-1-[2-(4-amidinobenzamido)-3-(4-methoxyphenyl) propionyl]-piperidin-4-yloxyacetate (Example 40) at pH=12 there is obtained, after chromatography (LiChroprep RP-18, water/methanol gradient) and crystallization from ethanol/ water, 0.05 g of (S)-1-[2-(4-amidinobenzamido)-3-(4-methoxyphenyl)propionyl]piperidin-4-yloxyacetate, m.p. 191°–192° C. MS (ISP): 483.3 (M+H)$^+$.

EXAMPLE 42

From 1.6g of t-butyl [1-[N-(4-amidinobenzoyl)-L-tryptophanyl]piperidin-4-yloxy]acetate there is obtained, in analogy to Example 1, after chromatography (LiChroprep RP-18, water/methanol gradient) and trituration with THF and aceto-nitrile, 0.7 g of [1-[N-(4-amidinobenzoyl)-L-tryptophanyl]-piperidin-4-yloxy]acetic acid, m.p. 210° C. (decomposition). MS (ISP): 492.2 (M+H)$^+$.

The ester starting material is prepared as follows:

a) Reaction of 5.1 g of t-butyl 4-piperidinyloxyacetate (Example 1c) with 8.0 g of Z-Trp-OH in the presence of HBTU and N-methylmorpholine, as described in Example 2b), yields, after chromatography (silica gel, methylene chloride/methanol 20:1), 11.5 g of t-butyl [1-(N-benzyloxycarbonyl-L-tryptophanyl)piperidin-4-yloxy]acetate, MS (ISP): 536.0 (M+H)$^+$.

b) A solution of 6.6 g of the product of a) in methanol is heated to boiling temperature in the presence of 10 percent Pd/C and ammonium formate. After filtration and chromatography (silica gel, methylene chloride/methanol 9:1) there are obtained 4.3 g of t-butyl (1-L-tryptophanyl-piperidin-4-yloxy)acetate. MS (EI): 384 (M—NH$_3$)$^+$.

c) By reacting 1.9 g of the product of b) with 1.15 g of 4-amidinobenzoyl chloride hydrochloride in pyridine, as described in Example 1f), there are obtained, after chromatography (silica gel, methylene chloride/methanol 7:1), 1.6 g of ester starting material, MS (ISP): 548.3 (M+H)$^+$.

EXAMPLE 43

A solution of 3.2 g of t-butyl 1-[N-(4-amidinobenzoyl)-4'-hexloxy-L-phenylalanyl]piperidin-4-yloxy]acetate in formic acid is left at room temperature overnight. After concentration, chromatography (LiChroprep RP-18, water/methanol gradient) and trituration with diethyl ether, there is isolated 0.45 g of [1-[N-(4-amidinobenzoyl)-4'-hexyloxy-L-phenylalanyl]piperidin-4-yloxy]acetic acid, m.p. 160° C. (decomposition). $[\alpha]_D^{20}$=+3.2° (c=0.5, methanol). MS (ISP): 553.2 (M+H)+.

The ester starting material is prepared as follows:

a) In analogy to Example 38a), the reaction of 5.6 g of t-butyl [[1-[N-(benzyloxycarbonyl)-L-tyrosyl]-4-piperidinyl]oxy]acetate with 1-iodohexane at 80° C. gives, after chromatography (silica gel, hexane/ethyl acetate 2.5:1), 3.9 g of t-butyl [1-(N-benzyloxycarbonyl-4'-hexyloxy-L-phenylalanyl) piperidin-4-yloxy]acetate, MS (EI): 445 (M—Z—NH$_2$)$^+$.

b) By hydrogenating 3.9 g of the product of a) in methanol, analogously to Example 1c), there are obtained 2.85 g of t-butyl [1-(4'-hexyloxy-L-phenylalanyl)piperidin-4-yloxy]acetate, MS (EI): 462 (M)$^+$, 445 (M—NH$_3$)$^+$.

c) By reacting 0.5 g of the product of b) with 0.3 g of 4-amidinobenzoyl chloride hydrochloride in pyridine, analogously to Example 1f), there is obtained, after chromatography (silica gel, methylene chloride/methanol 5:1), 0.7 g of ester starting material, MS (ISP): 609.4 (M+H)$^+$.

EXAMPLE 44

A solution of 0.65 g of t-butyl (R,S)-1-[2-(4-aminoiminomethyl-N-methylbenzoylamino)-3-(4-methoxyphenyl)propionyl]piperidin-4-yloxy]acetate in formic acid is left at room temperature overnight. After concentration and chromatography (LiChroprep RP-18, water/acetonitrile gradient), there is isolated 0.13 g of (R,S)-1-[2-(4-aminoiminomethyl-N-methylbenzoylamino)-3-(4-methoxyphenyl)propionyl]piperidin-4-yloxy]acetic acid, m.p. 181°–182° C. MS (ISP): 497.1 (M+H)$^+$.

The ester starting material is prepared as follows:

a) By coupling 1.38 g of Z-N-Me-Tyr(Me)-OH (J.A.C.S., 112, 1990, 7663) with 0.86 g of t-butyl 4-piperidinyloxyacetate (Example 1c) there are obtained, as described in Example 2b), after chromatography (silical gel, diethyl ether/hexane 5:1), 1.6 g of t-butyl (R,S)-1-[2-(N-benzyloxycarbonyl-N-methylamino)-3-(4-methoxyphenyl)propionyl]piperidin-4-yloxy]-acetate, MS (EI): 541.0 (M+H)$^+$.

b) By hydrogenating 1.5 g of the product of a) in methanol, as described in Example 1c), there are obtained 1.05 g of an oil which is reacted directly with 0.58 g of 4-amidinobenzoyl chloride hydrochloride in pyridine as described in Example 1f). After chromatography (silica gel, methylene chloride/methanol 9:1), there is obtained 0.7 g of ester starting material, m.p. 109°–111° C. MS (ISP): 553.2 (M+H)$^+$.

EXAMPLE 45

By esterifying 0.07 g of (R,S)-1-[2-(4-aminoiminomethyl-N-methylbenzoylamino)-3-(4-methoxyphenyl)propionyl]piperidin-4-yloxyacetic acid in ethanol, as described in Example 34, there is obtained, after chromatography (LiChroprep RP-18, water/ethanol gradient) and trituration with diethyl ether, 0.056 g of ethyl (R,S)-1-[2-(4-aminoiminomethyl-N-methylbenzoylamino)-3-(4-methoxyphenyl) propionyl] piperidin-4-yloxyacetate, m.p. 126°–128° C. MS (ISP): 525.5 (M+H)$^+$.

EXAMPLE 46

5 ml of trifluoroacetic acid are added to 100 mg of t-butyl (S,)-cis-1-[2-(4-amidinobenzoylamino)propionyl]-4-t-butoxycarbonylmethoxy-pyrrolidin-3-yloxyacetate in 5 ml of methylene chloride. After stirring at room temperature, the solvent is evaporated and the residue is chromatographed on silica gel RP-18 with water/THF (0–50%). There are obtained 73 mg of (S)-cis-1-[2-(4-amidinobenzoylamino) propionyl]-4-carboxymethoxy-pyrrolidin-3-yloxyacetic acid. MS: 437 (M+H)$^+$.

The ester starting material is prepared as follows:

a) 237 mg of cis-N-benzyloxycarbonylpyrrolidine-3,4-diol, 1 ml of t-butyl bromoacetate and 100 mg of tetrabutyl-ammonium hydrogen sulphate in 10 ml of toluene are stirred with 10 ml of 50% sodium hydroxide solution under phase transfer conditions. The organic phase is washed with water and evaporated. Chromatography of the evaporation residue on silica gel with ethyl acetate/hexane (1:3) gives 354 mg of benzyl cis-3,4-bis-t-butoxycarbonylmethoxy-pyrrolidine-1-carboxylate. MS: 354 (M-111).

b) 320 mg of the product of the previous step in 10 ml of EtOH are hydrogenated in the presence of 100 mg of 10% Pd/C, the catalyst is filtered off after 2 hours and the residue in 10 ml of THF is stirred with 224 mg of N-benzyloxycarbonyl-L-alanine N-hydroxysuccinimide ester in the presence of 100 µl of triethylamine. The reaction solution is diluted with ether, the organic phase is washed with 1M KHSO$_4$ solution, dried and evaporated. Chromatography of the residue on silica gel with hexane/ethyl acetate (1:1) gives 260 mg of t-butyl (S)-cis-1-(2-benzyloxycarbonylamino-propionyl)-4-t-butoxycarbonylmethoxy-pyrrolidin-3-yloxyacetate. MS: 537 (M+H)$^+$.

c) 250 mg of the product of the preceding step are hydrogenated in 10 ml of EtOH in the presence of 100 mg of 10% Pd/C, the catalyst is filtered off after 4 hours and the residue in 10 ml of pyridine is stirred with 102 mg of p-amidinobenzoyl chloride hydrochloride. Evaporation of the solution and chromatography of the residue on silica gel RP-18 with water/THF (5–30%) gives 143 mg of ester starting material, m.p. 127° C. (d).

EXAMPLE 47

A solution of 150 mg of ethyl (S)-8-[2-(4-aminoiminomethyl-benzoylamino)-3-(4-t-butoxyphenyl)propionyl]-8-azabicyclo[3.2.1]octan-endo-3-yloxyacetate hydrochloride is stirred at room temperature in 5 ml of $CH_2C_2$ and 2.5 ml of trifluoroacetic acid and evaporated. With ether the residue gives crystals which are filtered off under suction and dissolved in 5 ml of EtOH. 40 mg of NaOH dissolved in 1 ml of water are added to the solution and the mixture is stirred at room temperature. The reaction solution is neutralized with 1N hydrochloric acid and evaporated. Chromatography of the residue on silica gel RP-18 with water/THF gives 75 mg of (S)-8-[2-(4-aminoiminomethyl-benzoylamino)-3-(4-hydroxyphenyl)propionyl]-8-azabicyclo[3.2.1]octan-endo-3-yloxyacetic acid. MS: 495 (M+H)$^+$.

The ester starting material is prepared as follows:

a) 2 ml of ethyl diazoacetate in 2 ml of toluene are added at 80° C. to a solution of 1 g of N-benzyloxycarbonyl-nortropine and 20 mg of rhodium(II) acetate in 3 ml of toluene. After 3.5 hours, the solution is evaporated and the residue is chromatographed on silica gel with hexane/ethyl acetate (20–50%). There are obtained 555 mg of benzyl endo-3-ethoxy-carbonylmethoxy-8-azabicyclo[3.2.1]octan-8-carboxylate. MS: 348 (M+H)$^+$.

b) A solution of 500 mg of the product of the preceding step in 20 ml of EtOH is hydrogenated in the presence of 100 mg of 10% Pd/C, the catalyst is filtered off after 3 hours and the filtrate is evaporated. The residue is dissolved in 10 ml of THF and added to a solution of 828 mg of N-Z-L-Tyr(tBu)-OH, 140 µl of N-methylmorpholine and 569 mg of HBTU in 10 ml of THF which has been stirred at 0° C. for 1 hour. After stirring, the reaction solution is evaporated and the residue is chromatographed on silica gel with hexane/ethyl acetate (1). The are obtained 650 mg of ethyl (S)-8-[2-benzyloxy-carbonylamino-3-(4-t-butoxyphenyl)propionyl]-8-azabicyclo[3.2.1]octan-endo-3-yloxyacetate. MS: 567 (M+H)$^+$.

c) 600 mg of the product of the previous step are hydrogenated in 20 ml of EtOH in the presence of 100 mg of 10% Pd/C, the catalyst is filtered off after 16 hours and the residue in 10 ml of pyridine is stirred at room temperature with 262 mg of p-amidinobenzoyl chloride hydrochloride. Evaporation of the solution and chromatography of the residue on silica gel RP-18 with water/THF (0–50%) gives 198 mg of ester starting material. MS: 579 (M+H)$^+$.

EXAMPLE 48

706 mg of butyl (E)- or (Z)-(S)-[3-[2-[4-(t-butoxycarbonylimino-di-t-butoxycarbonylaminomethyl)benzoyl-amino]propionylamino]propoxy]acetate are stirred at 20° C. in 1.5 ml of methylene chloride and 1.5 ml of trifluoroacetic acid. After evaporation of the solvent in a vacuum, evaporation with toluene and crystallization from acetonitrile, there are obtained 407 mg of butyl (S)-[3-[2-[4-(aminoiminomethyl)benzoyl-amino]propionylamino]propoxy]acetate trifluoroacetate (1:1), m.p. 163°–165° C., $[\alpha]_D^{20}=+19°$ (c=0.5 in methanol).

The starting material is obtained in the following manner:

a) Acrylonitrile, butyl glycolate and potassium carbonate are heated to 60° C. After working up with ethyl acetate and water, the butyl 2-cyanoethoxyacetate is distilled. B.p. 100°–120° C., 0.03 mm Hg (bulb-tube).

b) This is hydrogenated in acetic acid on Pd/C and the amine which thereby results is coupled with N-benzyloxycarbonyl-L-alanine to give butyl (S)-[3-(2-benzyloxycarbonylaminopropionylamino)propoxy]acetate, m.p. 54°–55° C., $[\alpha]_D^{20}=-11.0°$ (c=0.5 in methanol).

c) By hydrogenation on Pd/C in acetic acid there is obtained therefrom butyl [3-(2-aminopropionylamino)propoxy]acetate which is coupled with p-[E/Z]-tri(t-butoxycarbonyl)amidinobenzoic acid to give the starting material. MS: 707 (27 M+H), $[\alpha]_D^{20}=+21.4°$ (c=0.5 in methanol).

EXAMPLE 49

416 mg of butyl (S)-[3-[2-[4-(aminoiminomethyl)benzoylamino]propionylamino]propoxy]acetate are stirred at 20° C. in 8.3 ml of 25 percent hydrochloric acid. The solution is evaporated and the residue is evaporated with water. From THF there are obtained 211 mg of (S)-[3-[2-[4-(aminoimino-methyl) benzoylamino]propionylamino]propoxy]acetic acid hydrochloride as the hydrate (1:1), m.p. 89°–90° C., $[\alpha]_D^{20}=+23.4°$ (c=0.5 in methanol).

EXAMPLE 50

1 g of tert-butyl 1-[N-[4-(t-butoxycarbonylimino-di-t-butoxycarbonylaminomethyl)benzoyl]-N-(2-methoxyethyl)glycyl]piperidin-4-yloxyacetate is stirred at 20° C. in 3.8 ml of methylene chloride and 3.8 ml of trifluoroacetic acid. The solvent mixture is evaporated, the residue is evaporated with water, dissolved in ethyl alcohol and adjusted to pH 8 with methanolic ammonia solution, whereupon 1-[N-[4-(aminoiminomethyl) benzoyl]-N-(2-methoxyethyl)glycyl]piperidin-4-yloxy-acetic acid crystallizes out as the hydrate (2:1). M.p. >250° C. MS: 421 (100, M+H).

The ester starting material can be obtained in the following manner:

a) N-(2-Methoxyethyl)glycine t-butyl ester is converted with benzyl chloroformate in ether and saturated aqueous sodium bicarbonate solution into N-benzyloxycarbonyl-N-(2-methoxyethyl)glycine t-butyl ester, MS: 324 (82, M+H).

b) This is cleaved in methylene chloride/trifluoroacetic acid to N-benzyloxycarbonyl-N-(2-methoxyethyl)glycine, MS: 267 (1, M).

c) Coupling of the latter with t-butyl piperidin-4-yloxy-acetate leads to t-butyl 1-[N-benzyloxycarbonyl-N-(2-methoxy-ethyl) glycyl]piperidin-4-yloxyacetate, MS: 465 (100, M+H).

d) By catalytic hydrogenation on Pd/C in ethanol there is obtained therefrom t-butyl 1-[N-(2-methoxyethyl) glycyl]-piperidin-4-yloxyacetate, MS: 331 (100, M+H).

e) This is coupled with 4-(t-butoxycarbonylimino-di-t-butoxycarbonylaminomethyl)benzoic acid to give the ester starting material, MS: 777 (70, M+H).

EXAMPLE A

A compound of formula I can be used in a known manner as the active ingredient for the production of tablets of the following composition:

|  | Per tablet |
| --- | --- |
| Active ingredient | 200 mg |
| Microcrystalline cellulose | 155 mg |
| Maize starch | 25 mg |
| Talc | 25 mg |
| Hydroxypropylmethylcellulose | 20 mg |
|  | 415 mg |

EXAMPLE B

A compound of formula I can be used in a known manner as the active ingredient for the manufacture of capsules of the following composition:

|  | Per capsule |
| --- | --- |
| Active ingredient | 100.0 mg |
| Maize starch | 20.0 mg |
| Lactose | 95.0 mg |
| Talc | 4.5 mg |
| Magnesium stearate | 0.5 mg |
|  | 220.0 mg |

We claim:

1. A compound of the formula

   I wherein

L is a group of the formula

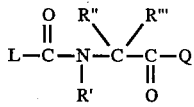   $L^1$ or

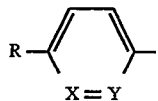   $L^2$

R is amidino or guanidino, one of X and Y is CH, and the other is N, $R^o$ is hydrogen or amidino, t is an integer between 2 and 6, R', R" and R'", in the α-aminocarboxylic acid residue of the formula —N(R')C(R",R'")CO—, are hydrogen or N-substituents R' or sidechains R" and R'" of open chain or cyclic, natural or synthetic α-aminocarboxylic acids, wherein a hydroxy or carboxy group present in the N-substituent R' and sidechains R" and R'" can be etherified or, respectively, esterified or amidated, and amino groups can be $C_{1-6}$ alkanoylated or aroylated, and wherein R' and R" together with the N atom and C atom to which they are attached can form a 4- to 6-membered ring;

Q is a group of the formula

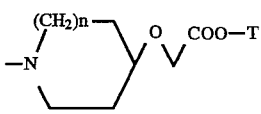   $Q^1$

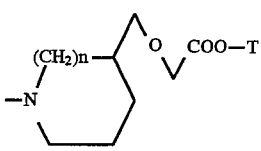   $Q^2$

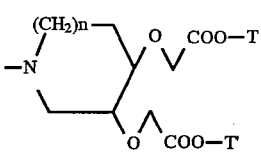   $Q^3$

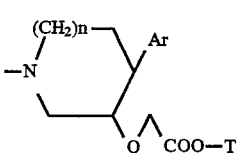   $Q^5$ or

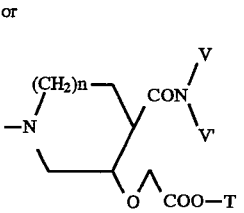   $Q^6$ n is the number 1,

T and T' are hydrogen or a lower-alkyl or phenyl-lower-alkyl group which is cleavable under physiological conditions, V and V' are hydrogen or lower-alkyl, Ar is phenyl or phenyl substituted with up to three substituents selected from the group consisting of alkyl, hydroxy, lower-alkoxy, halogen and halo-lower alkyl, as well as hydrated or solvates and physiologically usable salts thereof.

2. A compound according to claim 1, wherein L is a group $L^1$, and T in the group Q is hydrogen or a lower-alkyl group cleavable under physiological conditions.

3. A compound according to claim 2, wherein L is a group $L^1$, R is amidino, X is CH, Y is N, and Q is a group $Q^1$, $Q^2$, or $Q^5$.

4. A compound according to claim 1, 2 or 3, wherein Q is a group $Q^1$, n=1 and T is hydrogen or methyl, and —N(R')C(R",R'") CO— is a residue selected from the group consisting of Gly, Ala, D-Ala, Val, Leu, Sar, Orn, Lys, Phg, 2-methyl-Pro, Phe, Tyr, 3-iodo-Tyr, 3,5-diiodo-Tyr, Ser(Ac), Ser, Asp, Glu, Pro, 4-benzyloxy-Pro, 4-hydroxy-Pro, 2-piperidylenecarbonyl, NHCH($CH_2CH_2NH_2$)CO, Trp, Tyr (Me), Tyr(hexyl) and O,N(Me)$_2$-Tyr.

5. A compound according to claim 1, 2 or 3, wherein Q is a group $Q^2$, n=1, T is hydrogen and —N(R')C(R",R'")CO— is the Ala residue.

6. A compound according to claim 1, 2 or 3, wherein Q is a group $Q^5$, n=1, T is hydrogen, Ar is α,α,α-trifluoro-m-tolyl and —N(R')C (R",R'")CO— is the Ala residue.

7. A compound according to claim 1, wherein Q is a group $Q^3$, n=0 and T is hydrogen.

8. A compound according to claim 1, wherein —N(R')C (R",R'")CO— is the N(methoxyethyl)Gly residue.

9. A compound according to claim 1, selected from the group consisting of:

[[1-[N-[(5-amidino-2-pyridyl)carbonyl]-L-alanyl]-4-piperidinyl]oxy]acetic acid, and

[[1-[N-[(5-amidino-2-pyridyl)carbonyl]-L-tyrosyl]-4-piperidinyl]oxy]acetic acid.

10. A compound according to claim 1, (S)-1-[2-(5-Amidinopyridin-2-ylcarbonylamino)-3-(4-methoxyphenyl)propionyl]piperidin-4-yloxyacetic acid.

11. A compound of the formula

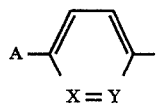   II or

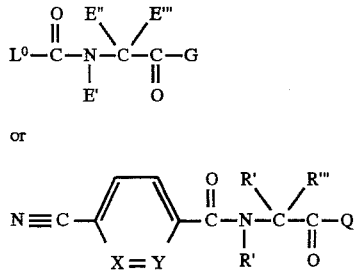   III wherein $L^o$ is a group of the formula

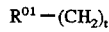   $L^{o1}$ or $R^{o1}-(CH_2)_t$   $L^{o2}$ in which

A is an optionally protected amidino or guanidino group, $R^{o1}$ is an optionally protected amino or guanidino group, one of X and Y is CH and the other is N, t is an integer between 2 and 6, R', R", R'", E', E" and E'" in the α-aminocarboxylic acid residue of the formula N(R')C(R",R'")CO— or N(E')C(E",E'")CO—, are hydrogen or N- substituents R' or E' or sidechains R" and R'" or E" and E'" of open chain or cyclic, natural or synthetic α-aminocarboxylic acids, wherein a hydroxy or carboxy group present in the N-substituent R' or E' and sidechains R" and R'" or E' and E'" can be etherified or, respectively, esterified or amidated, and amino groups can be $C_{1-6}$ alkanoylated or aroylated, and wherein R' and R" or E' and E" together with the N atom and C atom to which they are attached can form a 4- to 6- membered ring;

Q and G are each a group of the formula

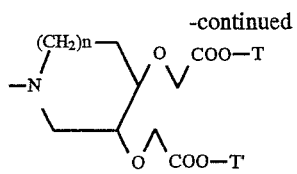   $Q^1$

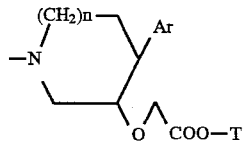   $Q^2$

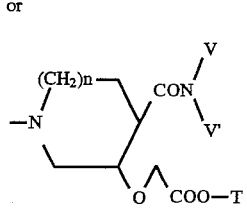   $Q^3$

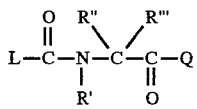   $Q^5$ or

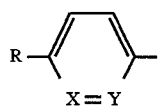   $Q^6$ n is the number 1,

T and T' are hydrogen or lower-alkyl or phenyl-lower-alkyl group which is cleavable under physiological conditions, V and V' are hydrogen or lower-alkyl, Ar is phenyl or phenyl substituted with up to three substituents selected from the group consisting of alkyl, hydroxy, lower-alkoxy, halogen and halo-lower alkyl, with the proviso that where $R^{o1}$ is amino or guanidino or where A is amidino or guanidino, at least one of E', E", E'" and G contains at least one carboxylic acid ester group and/or ether group and/or protected amino group.

12. A pharmaceutical composition comprising an effective amount of a compound of the formula

   I wherein

L is a group of the formula

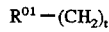   $L^1$ or $R^o-NH(CH_2)_t$   $L^2$

R is amidino or guanidino, one of C and Y is CH, and the other is N, $R^o$ is hydrogen or amidino, t is an integer between 2 and 6, R', R" and R'", in the α-aminocarboxylic acid residue of the formula —N(R')C(R", R'")CO—, are hydrogen or N-substituents R' or sidechains R" and R'" of open chain or cyclic, natural or synthetic α-aminocarboxylic acids, wherein a hydroxy or carboxy group present in the N-substituent R' and sidechains R" and R'" can be etherified or, respectively, esterified or amidated, and amino groups can be $C_{1-6}$ alkanoylated or aroylated, and wherein R' and R" together with the N atom and C atom to which they are attached can form a 4- to 6-membered ring;

Q is a group of the formula

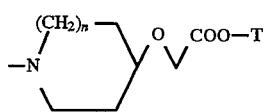 Q¹

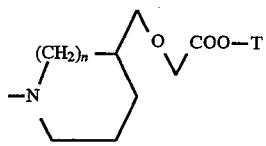 Q²

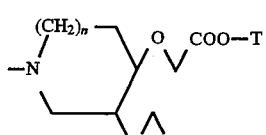 Q³

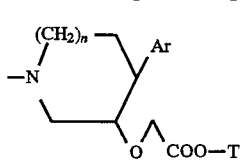 Q⁵ or

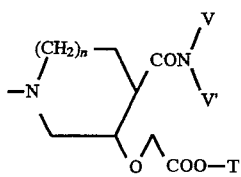 Q⁶ n is the number 1,

T and T' are hydrogen or a lower-alkyl or phenyl-lower alkyl group which is cleavable under physiological conditions, V and V' are hydrogen or lower-alkyl, Ar is phenyl or phenyl substituted with up to three substituents selected from the group consisting of alkyl, hydroxy, lower-alkoxy, halogen and halo-lower alkyl, as well as hydrates or solvates and physiologically usable salts thereof and a pharmaceutically inert carrier.

13. The pharmaceutical composition according to claim 12, wherein L is a group L¹ and T in the group Q is hydrogen or a lower-alkyl group cleavable under physiological conditions.

14. The pharmaceutical composition according to claim 13, wherein L is a group L¹, R is amidino, X is CH, Y is N, and Q is a group Q¹, Q², or Q⁵.

15. The pharmaceutical composition according to claim 12, 13 or 14, whereto Q is a group Q¹, n=1 and T is hydrogen or methyl, and —N(R')C(R",R''') CO— is a residue selected from the group consisting of Gly, Ala, D-Ala, Val, Leu, Sar, Orn, Lys, Phg, 2-methyl-Pro, Phe, Tyr, 3-iodo-Tyr, 3,5-diiodo-Tyr, Ser(Ac), Ser, Asp, Glu, Pro, 4-benzyloxy-Pro 4-hydroxy-Pro, 2-piperidylenecarbonyl, NHCH(CH₂CH₂NH₂)CO, Trp, Tyr (Me), Tyr(hexyl) and O,N(Me)₂-Tyr.

16. The pharmaceutical composition according to claim 12, 13 or 14, wherein Q is a group Q², n=1, T is hydrogen and —N(R')C(R",R''')CO— is the Ala residue.

17. The pharmaceutical composition according to claim 12, 13 or 14, wherein Q is a group Q⁵, n=1, T is hydrogen, Ar is α,α,α-trifluoro-m-tolyl and —N(R')C(R",R''') CO— is the Ala residue.

18. The pharmaceutical composition according to claim 12, wherein the compound of formula I is selected from the group consisting of

[[1-[N-[(5-amidino-2-pyridyl)carbonyl]-L-alanyl]-4-piperidinyl]oxy]acetic acid,

[[1-[N-[(5-amidino-2-pyridyl)carbonyl]-L-tyrosyl]-4-piperidinyl]oxy]acetic acid.

19. The pharmaceutical composition according to claim 12, wherein Q is a group Q³, n=0 and T is hydrogen.

20. The pharmaceutical composition according to claim 12, wherein —N(R')C(R",R''')CO— is the N(methoxyethyl) Gly residue.

21. The pharmaceutical composition according to claim 12 wherein the compound of formula I is (S)-1-[2-(5-Amidinopyridin-2-ylcarbonylamino)-3-(4-methoxyphenyl)propionyl]piperidin-4-yloxyacetic acid.

22. A method for the control or prevention of blood platelet thrombi, thrombosis, stroke, cardiac infarct, inflammation, or arteriosclerosis, comprising administering a compound of the formula

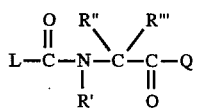 I wherein

L is a group of the formula

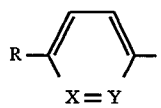 L¹ or

R°—NH(CH₂)ₜ  L²

R is amidino or guanidino, one of X and Y is CH, and the other is N,

R° is hydrogen or amidino, t is an integer between 2 and 6,

R', R" and R''', in the α-aminocarboxylic acid residue of the formula —N(R')C(R",R''')CO—, are hydrogen or N-substituent R' or sidechains R" and R''' of open chain or cyclic, natural or synthetic α-aminocarboxylic acids, wherein a hydroxy or carboxy group present in the N-substituent R' and sidechains R" and R''' can be etherified or, respectively, esterified or amidated, and amino groups can be $C_{1-6}$ alkanoylated or aroylated, and wherein R' and R" together with the N atom and C atom to which they are attached can form a 4- to 6-membered ring;

Q is a group of the formula

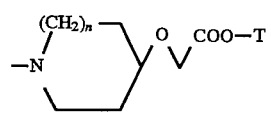 Q¹

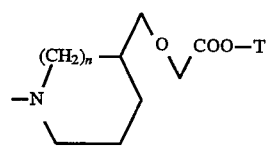 Q²

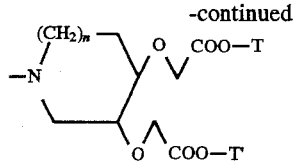   Q³

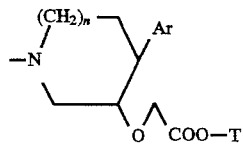   Q⁵ or

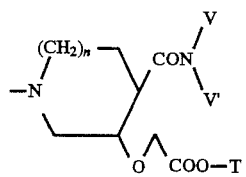   Q⁶ n is the number 1,

T and T' are hydrogen or a lower-alkyl or phenyl-lower alkyl group which is cleavable under physiological conditions, V to V' are hydrogen or lower-alkyl, Ar is phenyl or phenyl substituted with up to three substituents selected from the group consisting of alkyl, hydroxy, lower-alkoxy, halogen and halo-lower alkyl, as well as hydrates or solvates and physiologically usable salts thereof.

23. The method of claim 22, wherein L is a group $L^1$ and T in the group Q is hydrogen or a lower-alkyl group cleavable under physiological conditions.

24. The method of claim 22, wherein L is a group $L^1$, R is amidino, X is CH, Y is CH or N, and Q is a group $Q^1$, $Q^2$, or $Q^5$.

25. The method of claim 22, wherein Q is a group $Q^1$, n=1 and T is hydrogen or methyl, and —N(R')C(R",R'")CO— is a residue selected from the group consisting of Gly, Ala, D-Ala, Val, Leu, Sar, Orn, Lys, Phg, 2-methyl-Pro, Phe, Tyr, 3-iodo-Tyr, 3,5-diiodo-Tyr, Ser(Ac), Ser, Asp, Glu, Pro, 4-benzyloxy-Pro, 4-hydroxy-Pro, 2-piperidylenecarbonyl, NHCH(CH₂CH₂NH₂)CO, Trp, Tyr (Me), Tyr(hexyl) and O,N(Me)₂-Tyr.

26. The method of claim 22, wherein Q is a group $Q^2$, n=1, T is hydrogen and —N(R')C(R",R'")CO— is the Ala residue.

27. The method of claim 22, wherein Q is a group $Q^5$, n=1, T is hydrogen, Ar is α,α,α-trifluoro-m-tolyl and —N(R')C(R",R'")CO— is the Ala residue.

28. The method of claim 22, wherein the compound of formula I is selected from the group consisting of

[[1-[N-[(5-amidino-2-pyridyl)carbonyl]-L-alanyl]-4-piperidinyl]oxy]acetic acid and

[[1-[N-[(5-amidino-2-pyridyl)carbonyl]-L-tyrosyl]-4-piperidinyl]oxy]acetic acid.

29. The method of claim, 22, wherein Q is a group Q₃, n=0 and T is hydrogen.

30. The method of claim 22, wherein —N(R')C(R",R'") CO— is the N(methoxy-ethyl)Gly residue.

31. The method of claim 22, wherein the compound of formula I is:

(S)-1-[2-(5-Amidinopyridin-2-ylcarbonylamino)-3-(4-methoxyphenyl)propionyl]piperidin-4-yloxyacetic acid.

32. A method for inhibiting fibrinogen-, fibronectin- and the Willebrand Factor-dependent binding of tumor cells to a fibrinogen receptor of blood platelets comprising administering to a host in need of said inhibition a compound of the formula

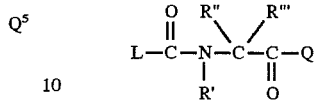   I wherein

L is a group of the formula

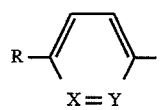   L¹ or

   L²

R is amidino or guanidino, one of X and Y is CH, and the other is N,

R° is hydrogen or amidino, t is an integer between 2 and 6,

R', R" and R'", in the α-aminocarboxylic acid residue of the formula —N(R')C(R",R'")CO—, are hydrogen or N-substituents R' or sidechains R" and R'" of open chain or cyclic, natural or synthetic α-aminocarboxylic acids, wherein a hydroxy or carboxy group present in the N-substituent R' and sidechains R" and R'" can be etherified or, respectively, esterified or amidated, and amino groups can be $C_{1-6}$ alkanoylated or aroylated, and wherein R' and R" together with the N atom and C atom to which they are attached can form a 4- to 6-membered ring;

Q is a group of the formula

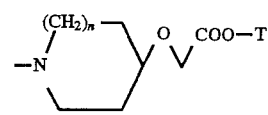   Q¹

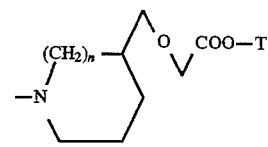   Q²

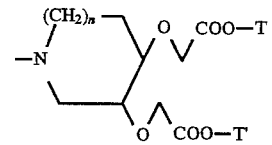   Q³

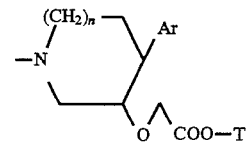   Q⁵ or

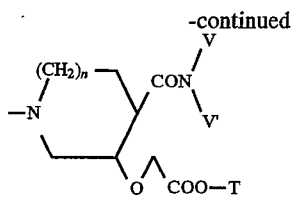

n is the number 1,

T and T' are hydrogen or a lower-alkyl or phenyl-lower alkyl group which is cleavable under physiological conditions, V and V' are hydrogen or lower-alkyl, Ar is phenyl or phenyl substituted with up to three substituents selected from the group consisting of alkyl, hydroxy, lower-alkoxy, halogen and halo-lower alkyl, as well as hydrates or solvates and physiologically usable salts thereof.

33. A method of wound healing comprising administering a compound of the formula

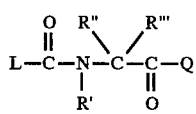   I wherein

L is group of formula

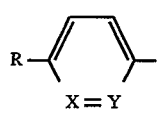   L¹ or

   L²

R is amidino or guanidino, one of X and Y is CH, and the other is N,

R° is hydrogen or amidino, t is an integer between 2 and 6,

R', R" and R'", in the α-aminocarboxylic acid residue of the formula —N(R')C(R",R'")CO—, are hydrogen or N-substituents R' or sidechains R" and R'" of open chain or cyclic, natural or synthetic α-aminocarboxylic acids, wherein a hydroxy or carboxy group present in the N-substituent R' and sidechains R" and R'" can be etherified or, respectively, esterified or amidated, and amino groups can be C₁₋₆ alkanoylated or aroylated, and wherein R' and R" together with the N atom and C atom to which they are attached can form a 4- to 6-membered ring;

Q is a group of the formula

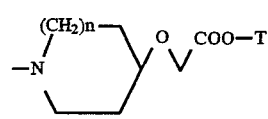   Q¹

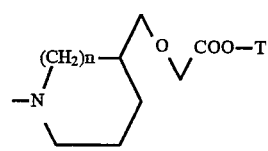   Q²

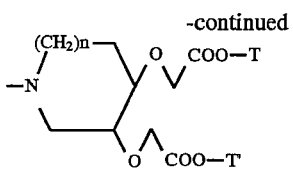   Q³

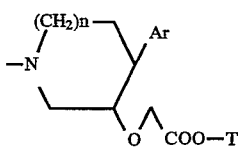   Q⁵ or

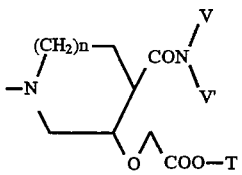   Q⁶ n is the number 1,

T and T' are hydrogen or a lower-alkyl or phenyl-lower alkyl group which is cleavable under physiological conditions, V and V' are hydrogen or lower-alkyl, Ar is phenyl or phenyl substituted with up to three substituents selected from the group consisting of alkyl, hydroxy, lower-alkoxy, halogen and halo-lower alkyl, as well as hydrates or solvates and physiologically usable salts thereof.

34. A method for treating osteoporosis comprising administering a compound of the formula

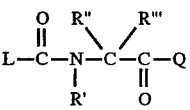   I wherein

L is a group of the formula

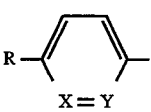   L¹ or

   L²

R is amidino or guanidino, one of X and Y is CH, and the other is N,

R° is hydrogen or amidino, t is an integer between 2 and 6,

R', R" and R'", in the α-aminocarboxylic acid residue of the formula —N(R')C(R",R'")CO—, are hydrogen or N-substituents R' or sidechains R" and R'" of open chain or cyclic, natural or synthetic α-aminocarboxylic acids, wherein a hydroxy or carboxy group present in the N-substituent R' and sidechains R" and R'" can be etherified or, respectively, esterified or amidated, and amino groups can be C₁₋₆ alkanoylated or aroylated, and wherein R' and R" together with the N atom and C atom to which they are attached can form a 4- to 6-membered ring;

Q is a group of the formula

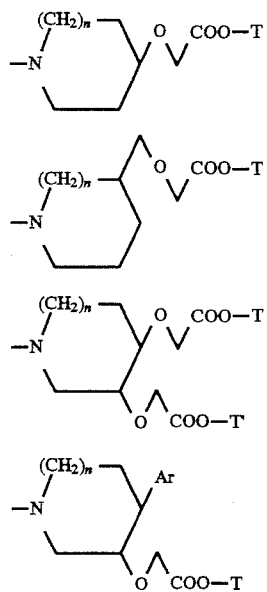

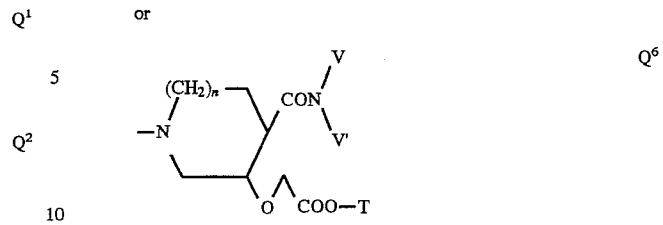

n is the number 1.

T and T' are hydrogen or a lower-alkyl or phenyl-lower alkyl group which is cleavable under physiological conditions, V and V' are hydrogen or lower-alkyl, Ar is phenyl or phenyl substituted with up to three substituents selected from the group consisting of alkyl, hydroxy, lower-alkoxy, halogen and halo-lower alkyl, and as well as hydrates or solvates and physiologically usable salts thereof.

* * * * *